US012806037B2

(12) United States Patent
Alden

(10) Patent No.: US 12,806,037 B2
(45) Date of Patent: Nov. 24, 2026

(54) PROSTHETIC COMPONENT EXTRACTOR

(71) Applicant: Kris Alden, Austin, TX (US)

(72) Inventor: Kris Alden, Austin, TX (US)

(*) Notice: Subject to any disclaimer, the term of this patent is extended or adjusted under 35 U.S.C. 154(b) by 1040 days.

(21) Appl. No.: 17/861,842

(22) Filed: Jul. 11, 2022

(65) Prior Publication Data

US 2022/0401230 A1 Dec. 22, 2022

Related U.S. Application Data

(63) Continuation-in-part of application No. 16/977,427, filed as application No. PCT/US2019/020437 on Mar. 1, 2019, now Pat. No. 11,382,766.

(60) Provisional application No. 62/637,075, filed on Mar. 1, 2018.

(51) Int. Cl.
*A61F 2/46* (2006.01)

(52) U.S. Cl.
CPC .... *A61F 2/4607* (2013.01); *A61F 2002/4619* (2013.01); *A61F 2002/4681* (2013.01)

(58) Field of Classification Search
CPC ... A61B 90/50; A61B 90/57; A61B 2090/571; A61B 17/02; A61B 17/0206; A61B 1/0014; A61B 5/6838; A61B 17/6441; A61B 17/6458; A61B 17/6466; A61B 2050/007; A61B 2050/0074; A61B 17/1327; A61B 17/92; A61F 2/4603; F16B 2/14
See application file for complete search history.

(56) References Cited

U.S. PATENT DOCUMENTS

| | | | | |
|---|---|---|---|---|
| 5,951,564 A * | 9/1999 | Schroder | A61F 2/4607 | 606/100 |
| 6,110,179 A * | 8/2000 | Flivik | A61B 17/8808 | 606/94 |
| 8,157,808 B2 * | 4/2012 | Keller | A61F 2/4607 | 606/89 |
| 8,657,834 B2 * | 2/2014 | Burgi | A61B 17/1659 | 606/99 |
| 2008/0208202 A1 * | 8/2008 | Williams | A61B 17/92 | 606/86 R |
| 2009/0143785 A1 * | 6/2009 | Chang | A61B 17/92 | 606/99 |

FOREIGN PATENT DOCUMENTS

| | | | |
|---|---|---|---|
| EP | 1845882 B1 * | 4/2015 | A61B 90/50 |
| EP | 3294155 B1 * | 11/2022 | A61B 17/1697 |

OTHER PUBLICATIONS

2015.*
2022.*

* cited by examiner

*Primary Examiner* — Anu Ramana

(57) ABSTRACT

A medical device, comprises an elongated member having a first end portion and a second end portion opposite the first end portion. A handle is coupled to the elongated member at the first end portion and defines a first striking surface. A second striking surface is coupled to the elongated member between the first end and the second end as a protrusion extending away from the elongated member. A hook is coupled to the second end portion and defines a channel sized and configured to receive at least a portion of a surgical implant.

7 Claims, 27 Drawing Sheets

Section C-C

PROSTHETIC COMPONENT EXTRACTOR

CROSS-REFERENCE TO RELATED APPLICATIONS

This application is a continuation-in-part of and claims priority to U.S. patent application Ser. No. 16/977,427, filed Sep. 1, 2020, entitled PROSTHETIC COMPONENT EXTRACTOR, issued as U.S. Pat. No. 11,382,766, which is a § 371 national phase entry of International Application No. PCT/US2019/020437, filed Mar. 1, 2019, which claims priority to U.S. Provisional Patent Application No. 62/637,075, filed Mar. 1, 2018, the entirety of all of which is incorporated herein by reference.

FIELD OF THE INVENTION

The present disclosure relates to systems and devices for extracting artificial joints, implants, or orthopedic prosthetics from the intramedullary cavity of a bone.

BACKGROUND OF THE INVENTION

Unless otherwise indicated herein, the materials described in this section are not admitted to be prior art to the claims in this application.

Load-carrying joints, such as the hip, can be rendered painful and thereby nonfunctional due to a multitude of disease states such as arthritis, fracture, or congenital deformity. The end result of the various pathophysiologic processes that impact a joint include degeneration, resulting in pain and loss of function for the individual. Joint replacement procedures with prosthetic implants have successfully treated and resolved numerous conditions that result in degeneration of affected joints. Due to both an aging population and younger patients desiring a more active lifestyle not impaired by degenerative conditions, joint replacement surgeries are becoming increasingly common.

In traditional procedures, implants can be affixed to the bone in one of two ways: (i) through cementing the implant into place, or (ii) through biologic fixation after impacting the implant into the medullary cavity of the bone. The un-cemented implants achieve bone ingrowth and integration onto the surface of the implant thereby obtaining biologic fixation. Knee, hip, and shoulder replacement procedures are the most commonly performed joint replacements worldwide. Hip implants, in particular, include an acetabular component, which is affixed to the pelvis, and a femoral component, which is secured to the proximal femur. The femoral component accepts a head component that articulates in a liner which is secured into the acetabular component.

The widespread adoption of orthopaedic implants to ameliorate degenerative joint conditions also has an important corollary: a variable percentage of prosthetic implants will ultimately fail. These prosthetic failures are due to a variety of etiologies including implant loosening, infection, dislocation, instability, and periprosthetic fracture. The failed implants must be removed during revision joint replacement procedures, whereby revision prosthetics allow for pain relief, mobility, and enhance the function of the individual. The current methodologies and tools available for the removal of prosthetics are generally rudimentary and have not evolved to facilitate modern and less invasive surgical techniques. The presently available implant removal tools require longer operative times, enlarged surgical dissection and incisions, and have less favorable success rates.

The bond that retains the component in the bone (either cement or biologic fixation) must be broken to facilitate removal of the failed implant. Should the current tools fail to achieve removal of the implant, surgical techniques to affect prosthetic removal include cutting the bone, i.e., performing an osteotomy. The revision joint replacement procedures that require an osteotomy are more invasive, of longer duration, require osteotomy healing, and significantly prolong recovery time for the patient. The physical work to remove well-fixed implants during a revision type surgical procedure can result in muscle, tissue, and bone damage, and thereby require longer operative times, reduce native host bone stock, increase the risk of postoperative surgical complications, and require longer patient recovery periods.

Commonly used surgical disimpaction techniques typically begin with the use of osteotomes to initially break the proximal bond between the implant and the host bone. This procedure and the instrumentation are generally limited in both the scope and depth of penetration. Once the maximal safe depth of penetration into the host bone is attained, further extraction techniques are required. Retrograde disimpaction of a femoral component through the employment of bone tamps can be used, but such a procedure is predicated on the implant having a collar or reasonable striking surface to impact and thereby dislodge the component. In addition, retrograde disimpaction may also require excessive bone removal and is generally ineffective due to the significant loss of force operating through an inferior angle through which the surgeon must direct force. Antegrade removal of a prosthetic implant is thereby the generally preferred surgical technique. Several modern prosthetic implants have a screw hole in the shoulder of the implant that can be used to affix an extraction device. However, these screw holes are generally inaccessible during the extraction phase of the revision joint replacement procedure and, therefore, are rarely helpful to effect extraction.

Attaching a lower profile extraction instrument with smaller dimensions to the trunnion of the femoral implant is a more facile approach to effect surgical removal. Such methods generally employ fixing an extractor to the proximal part of the prosthetic implant with pliers (or a similar instrument) and striking the instrument. Additionally, using a slaphammer device affixed to the implant to backslap the implant out of the bone can also be utilized. These devices are bulky, difficult to use, require greater surgical dissection, and generally do not permit the operator to generate sufficient force to break the bond between the implant and the host bone and thereby extract the implant.

SUMMARY

In view of the foregoing, it may be recognized that the above devices and methods are generally and practically ineffective in transmitting sufficient force to break the remaining bond between the implant and bone to thereby extract the prosthesis. Naturally, the force required to remove the implant must be less than the force that fixes the extractor to the implant, i.e. the fixation strength of the extractor to the implant must be greater than the force require to remove it. In the common scenario where the force required to remove the implant is greater than that achieved by the extractor, the extractor will ultimately fail to transmit sufficient force to the implant to effect its removal from the host bone. Therefore, a more facile, less invasive mechanism to exert force on the implant and thereby effect prosthetic implant removal may be desired.

Thus, in one embodiment, a device is provided. The device includes an elongated member having a first end and a second end, the elongated member comprising substantially straight, rod-like first, second, and third segments each having first and second ends, the first and second segments being connected by a first curved segment at their second and first ends, respectively, and the second and third segments being connected by a second curved segment at their second and first ends, respectively, and the first ends of each of the segments are proximal to the first end of the elongated member relative to the second ends of the segments. The device also includes a first striking surface positioned on the first segment extending away from the elongated member. The device also includes a second striking surface positioned on the third segment extending away from the elongated member. The device also includes a hook positioned at the second end of the third segment, wherein the hook includes a channel substantially perpendicular to a long axis of the third segment that is configured to engage a surgical implant.

According to one or more embodiments, a medical device, comprises an elongated member having a first end portion and a second end portion opposite the first end portion. A handle is coupled to the elongated member at the first end portion and defines a first striking surface. A second striking surface is coupled to the elongated member between the first end and the second end as a protrusion extending away from the elongated member. A hook is coupled to the second end portion and defines a channel sized and configured to receive at least a portion of a surgical implant.

In one aspect, the elongated member includes substantially straight first, second, and third segments each have first and second ends. The first and second segments are connected by a first curved segment at their second and first ends, respectively, and the second and third segments are connected by a second curved segment and a third curved segment joined together and disposed therebetween. The first end of each of the segments is proximal to the first end portion of the elongated member relative to the second ends of the segments.

In another aspect, the channel is oriented substantially perpendicular to a longitudinal axis of the third segment.

In another aspect, the second striking surface defines a plane substantially orthogonal to a longitudinal axis of the second segment.

In another aspect, the channel is oriented at an angle of about 130 degrees relative to the longitudinal axis of the third segment.

In another aspect, each of the first, second, and third segments, and the first, second, and third curved segments has a diameter of approximately 0.625 inches.

In another aspect, the second striking surface has at least one of: a length of approximately 2.5 inches; a width of approximately 1.5 inches; and a thickness of approximately 0.38 inches.

In another aspect, the hook is adjustable to change a width of the channel.

According to one or more embodiments is a hook for use with a medical device. The hook comprises a housing that defines a channel sized and configured to receive at least a portion of a surgical implant. A clamping arm is coupled to the housing at a pivot point and is configured to secure the surgical implant to the housing. An actuating element is disposed within the housing and is configured to move in a proximal-to-distal direction along an axis. The actuating element moves in the proximal-to-distal direction. The hook is configured to rotate about the pivot point.

In one aspect, the hook further includes a primary retaining mechanism releasably coupled to the housing. A secondary retaining mechanism is disposed within the housing and releasably coupled to the primary retaining mechanism. The secondary retaining mechanism is configured engage the actuating element within the housing.

In another aspect, the primary retaining mechanism and the secondary retaining mechanism are configured to advance towards a center of the housing when rotational forced is exerted on the primary retaining mechanism by a user.

In another aspect, advancement of the secondary retaining mechanism within the housing causes the actuating element to move in the proximal-to-distal direction.

In another aspect, the actuating element is a wedge block and the secondary retaining mechanism is a secondary locking bolt.

In another aspect, the surgical implant is a femoral implant having a body, a neck, and trunnion.

In another aspect, advancement of the actuating element towards a center of the housing causes the clamping arm to tighten the aperture around the trunnion of the surgical implant. Retraction of the actuating element away from the center of the housing lessens the tightness of the clamping arm around the trunnion.

In another aspect, the channel has a wall thickness of approximately 0.125 inches.

In another aspect, a wall thickness at a radius of the aperture is approximately 0.38 inches.

According to one or more embodiments, a medical system, comprises a medical device. The medical device includes an elongated member having a first end portion that defines a first striking surface and a second end portion opposite the first end portion. A hook is coupled to the elongated member at the second end portion. A second striking surface coupled to the elongated member between the first end portion and the second end portion as a protrusion extending away from the elongated member. A surgical implant is coupled to the medical device at the second end portion of the elongated member. The hook defines a channel sized and configured to releasably engage at least a portion of the surgical implant.

In one aspect, the elongated member includes substantially straight first, second, and third segments each having first and second ends. The first and second segments are connected by a first curved segment at their second and first ends, respectively, and the second and third segments are connected by a second curved segment and a third curved segment joined together and disposed therebetween. The first end of each of the segments are proximal to the first end portion of the elongated member relative to the second ends of the segments.

These as well as other aspects, advantages, and alternatives, will become apparent to those of ordinary skill in the art by reading the following detailed description, with reference where appropriate to the accompanying drawings.

DETAILED DESCRIPTION

Figure 1:
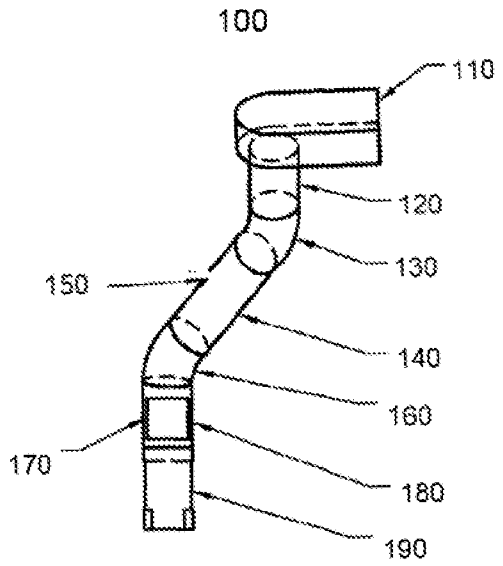
FIG. 1 illustrates a front view of an example device for a left hip, according to an example embodiment.
Figure 2:
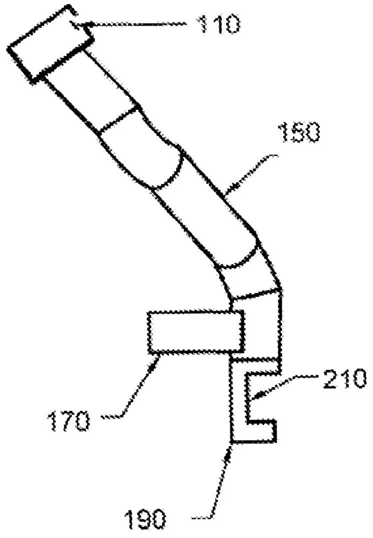
FIG. 2 illustrates a right-side view of the example device for a left hip of FIG. 1, according to an example embodiment.
Figure 3:
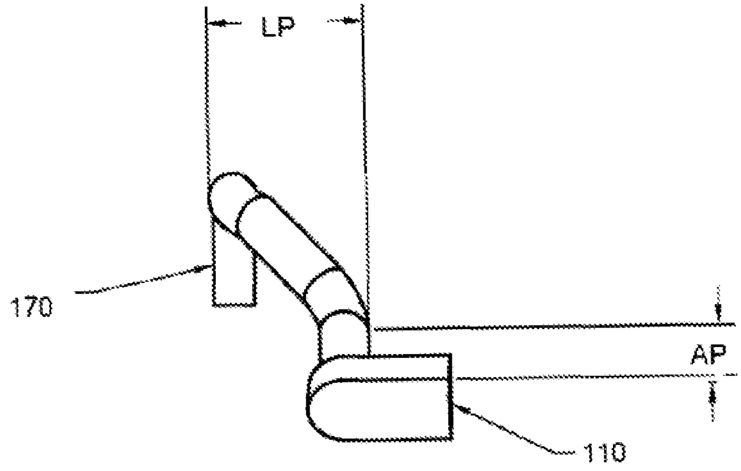
FIG. 3 illustrates a top view of the example device for a left hip of FIG. 1, according to an example embodiment.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Exemplary devices and systems are described herein. It should be understood that the word “exemplary” is used herein to mean “serving as an example, instance, or illustration.” Any embodiment or feature described herein as “exemplary” is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, “about” and “substantially” each means +/−5%.

As used herein, “coupled” means associated directly as well as indirectly. For example, a member A may be directly associated with a member B, or may be indirectly associated therewith, e.g., via another member C.

In the following description, numerous specific details are set forth to provide a thorough understanding of the disclosed concepts, which may be practiced without some or all of these particulars. In other instances, details of known devices and/or processes have been omitted to avoid unnecessarily complicating and obscuring the disclosure. While some concepts will be described in conjunction with specific examples, it will be understood that these examples are not intended to be limiting.

Unless otherwise indicated, the terms “first,” “second,” etc. are used herein merely as labels and are not intended to impose ordinal, positional, or hierarchical requirements on the items to which these terms refer. Moreover, reference to, e.g., a “second” item does not require or preclude the existence of, e.g., a “first” or lower-numbered item, and/or, e.g., a “third” or higher-numbered item.

As used herein, a system, apparatus, structure, article, element, component, or hardware “configured to” perform a specified function is capable of performing the specified function without any alteration, rather than merely having potential to perform the specified function after further modification. In other words, the system, apparatus, structure, article, element, component, or hardware “configured to” perform a specified function is specifically selected, created, implemented, utilized, programmed, and/or designed for the purpose of performing the specified function. As used herein, “configured to” denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being “configured to” perform a particular function may additionally or alternatively be described as being “adapted to” and/or as being “operative to” perform that function.

The present disclosure describes a prosthetic implant extraction device 100 to facilitate the surgical removal of a femoral component 270 of hip joint implant or intramedullary orthopaedic implant (cemented or uncemented intramedullary orthopaedic implants). The extractor device 100 described herein facilitates, tolerates, and transfers the high kinetic energy expended by the operator to the implant to disrupt the implant/bone interface and thereby affect the removal of the prosthetic component. In addition, the extractor device 100 is predicated on less invasive surgical techniques and exposure to minimize tissue and bone damage and optimize revision joint replacement procedures. As such, the present invention provides a more effective means to extract an implanted prosthetic component from the intramedullary canal. The overall goal achieved by the present invention is an efficient, less invasive, and facile means for extract an orthopaedic implant with a minimal amount of time, physical effort, and host tissue and bone damage.

In particular, the present disclosure provides a device 100 comprising (a) an elongated member 150 having a first end and a second end, the elongated member comprising substantially straight, rod-like first 120, second 140, and third 180 segments each having first and second ends, the first 120 and second 140 segments being connected by a first curved segment 130 at their second and first ends, respectively, and the second 140 and third 180 segments being connected by a second curved segment 160 at their second and first ends, respectively, and the first ends of each of the segments 120, 140 and 180 are proximal to the first end of the elongated member 150 relative to the second ends of the segments, (b) a first striking surface 110 positioned on the first segment 120 extending away from the elongated member 150, (c) a second striking surface 170 positioned on the third segment 180 extending away from the elongated member 150, and (d) a hook 190 positioned at the second end of the third segment 180, wherein the hook 190 includes a channel 210 substantially perpendicular to a long axis of the third segment 180 that is configured to engage a surgical implant.

Figure 7A:
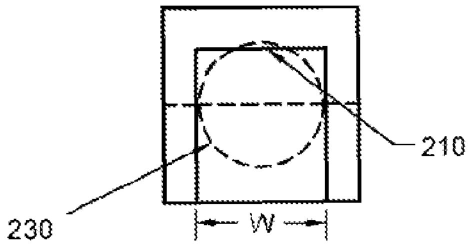
FIG. 7A illustrates a bottom view of a hook of the device of FIG. 1, according to an example embodiment.
Figure 7B:
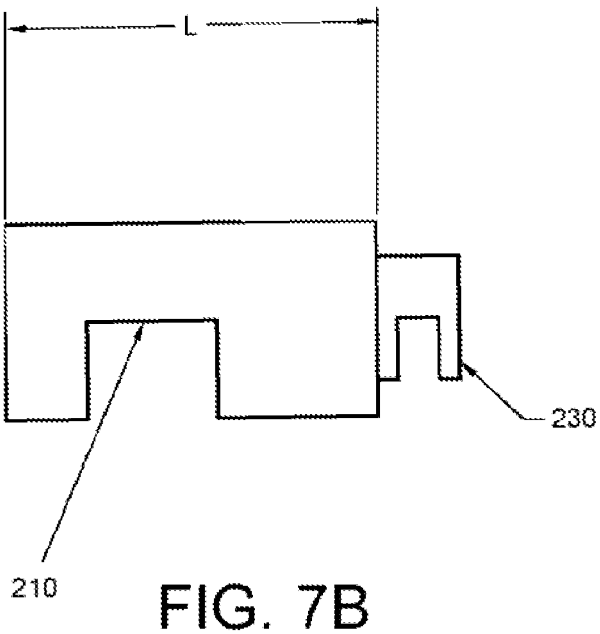
FIG. 7B illustrates a side view of the hook of FIG. 6A, according to an example embodiment.
Figure 8:
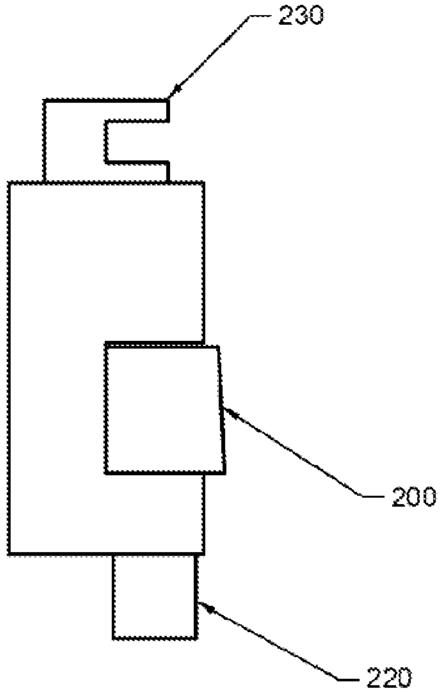
FIG. 8 illustrates a side view of the hook and lock of FIGS. 7A and 7B, according to an example embodiment.
Figure 9B:
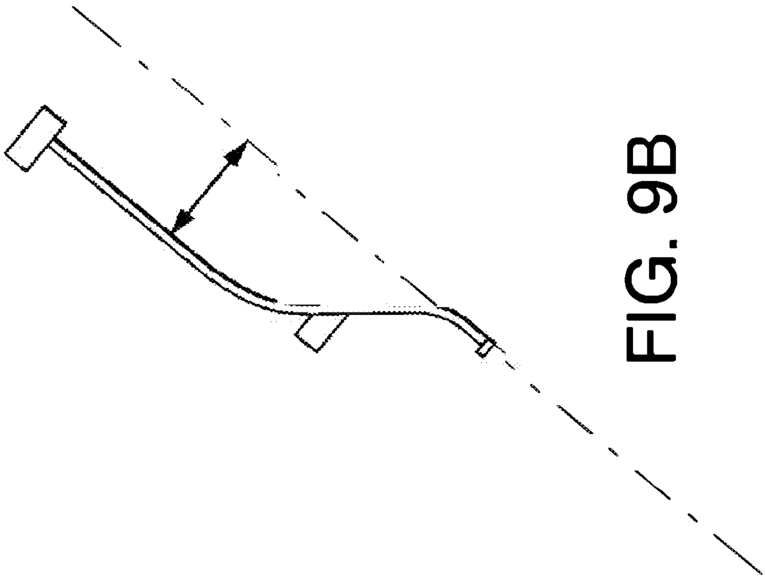
FIG. 9B illustrates a side view of another example device demonstrating the offset in the anterior plane, according to an example embodiment.
Figure 9A:
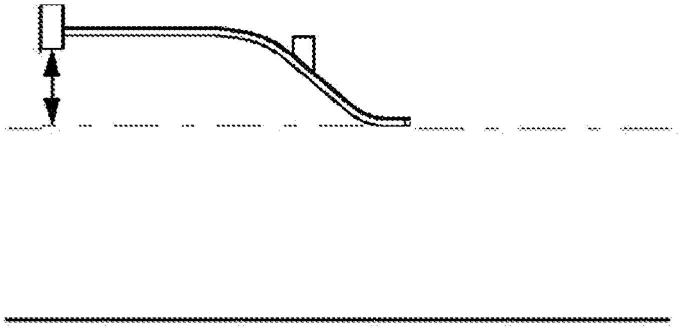
FIG. 9A illustrates a top view of another example device demonstrating the offset in the lateral plane, according to an example embodiment.
Figure 10:
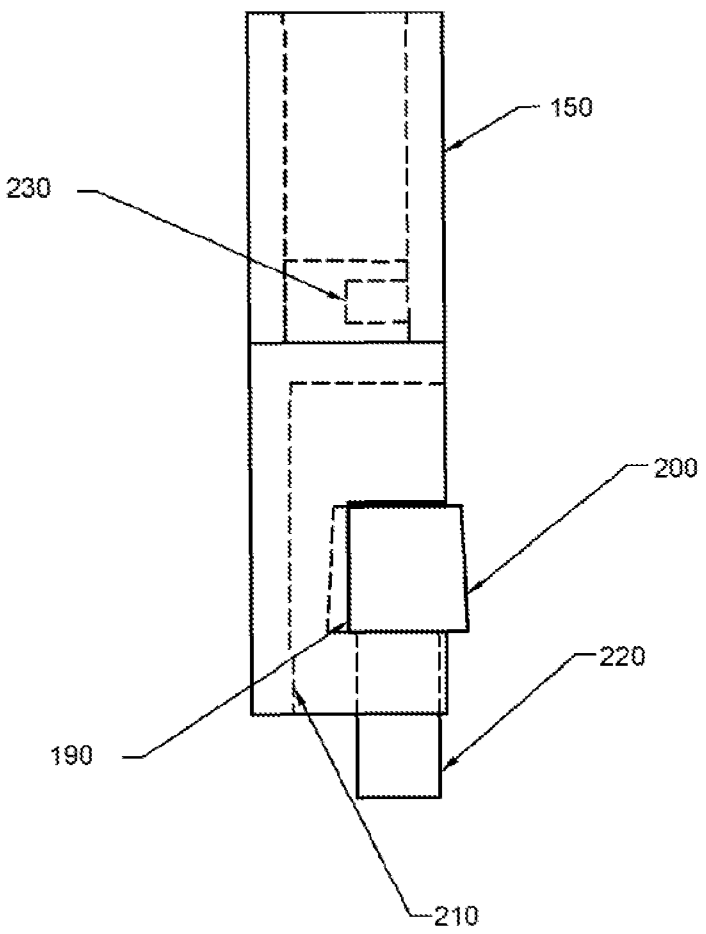
FIG. 10 illustrates a side view of the hook and lock, according to an example embodiment.
Figure 11:
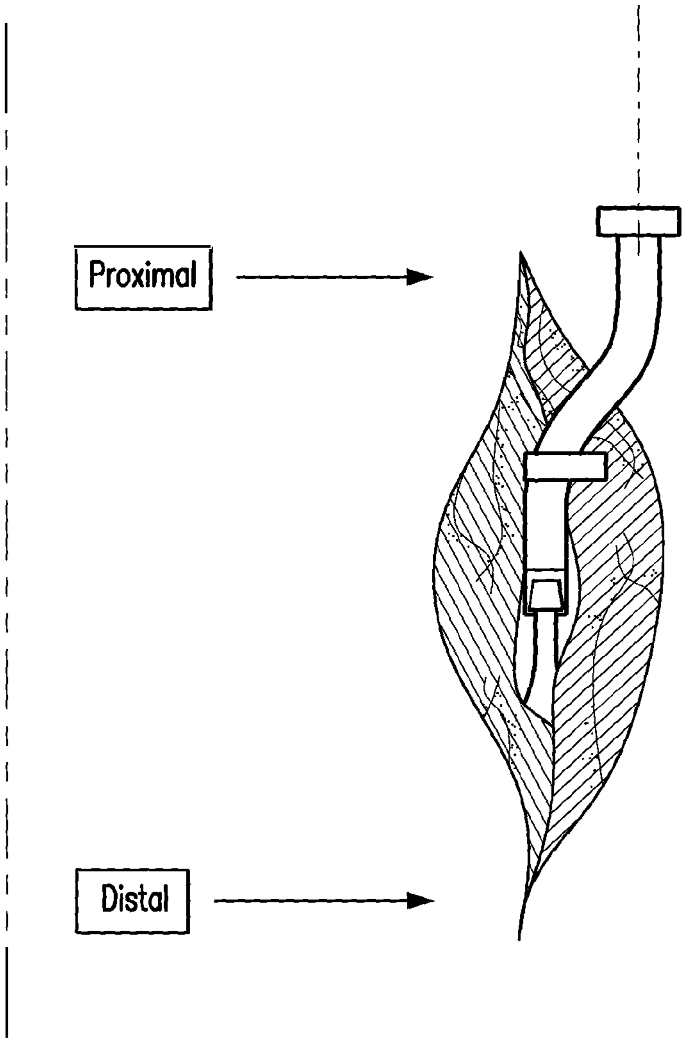
FIG. 11 illustrates a top view of the elongated member engaged with the hook and lock as it secures onto the trunnion of the femoral component, according to an example embodiment.
Figure 12:
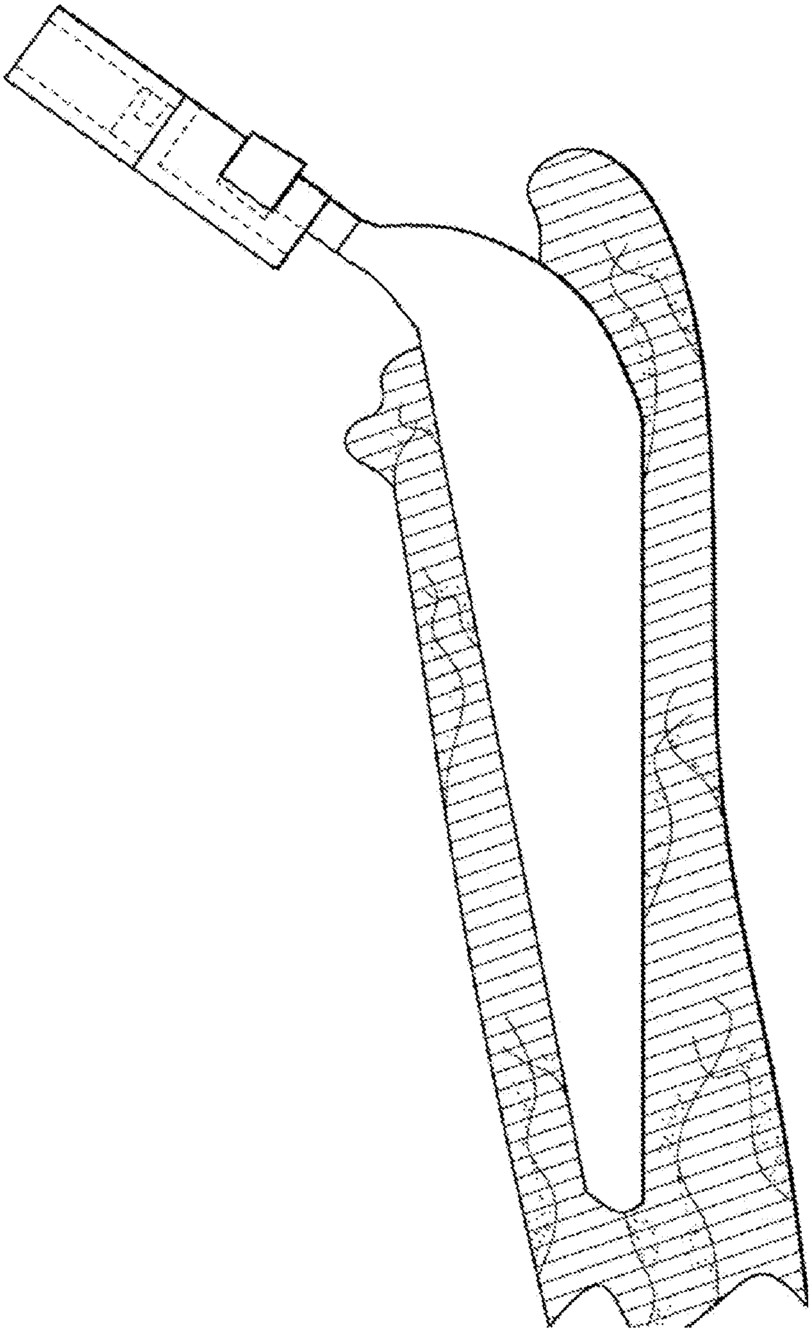
FIG. 12 illustrates a side view of the elongated member engaged with the hook and lock as it secures onto the trunnion of the femoral component, according to an example embodiment.
Figure 13:
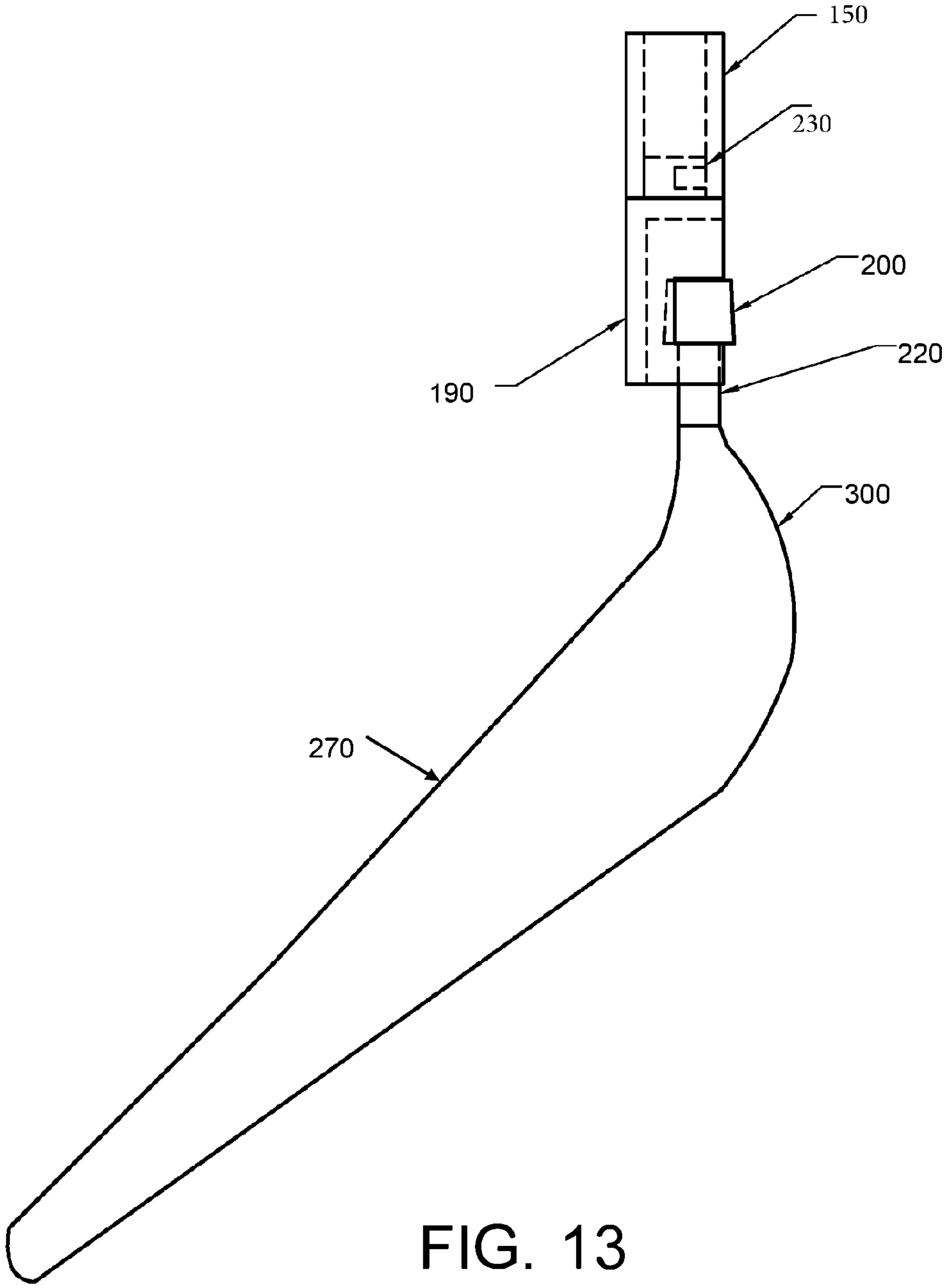
FIG. 13 illustrates a side view of the hook prior to engagement onto the trunnion of the femoral component and after engagement of the hook onto the trunnion, according to an example embodiment.

The hook 190 may be integrated into the second end of the third segment or modular and variably sized such that it can be secured to the neck 220 of the implant distal to the implant neck 220 or trunnion 200. Each such hook 190 may be configured for attachment to a specific stem implant having a known shape, size and geometry. The hook 190 may have a length (L) ranging from about 2 cm to about 4 cm. The length (L) of the hook is measured from a centerline extending into the hook starting at the proximal end (the end adjacent to the elongated member) and continuing to the distal end. As such, the length (L) of the hook is measured in a direction parallel to the long axis of the third segment 180 of the elongated member 150, as shown in FIGS. 1 and 7B. The variable sizes are optimized to a specific prosthesis and configured to be smaller than the trunnion section of the implant but larger than the neck of the prosthesis to provide for a secure mechanical coupling and grip of the proximal implant. In another embodiment, the hook channel width (W) is adjustable for engaging a specific prosthesis. In one embodiment, the channel is U-shaped such that a side of the hook is open to receive the neck of the prosthesis. In some embodiments, the channel of the hook may have a width (W) ranging from about 2 cm to about 3 cm. The width (W) is measured from a first interior surface of the channel to a second interior surface of the channel in a direction perpendicular to the long axis of the third segment of the elongated member, as shown in FIGS. 1 and 7A.

In one example, the hook 190 is permanently affixed to the second end of the elongated member 150. In another example, the hook 190 is removably coupled to the second end of the elongated member 150. In such embodiments, the device may include a lock 230 between the second end of the elongated member 150 and the hook 190. Preferably the lock 230 connects the hook 190 to the second end of the elongated member 150 such that there is little or no play between the two components. In one particular example, the hook 190 may include a clip, and the second end of the elongated member 150 may include a lever configured to mate with the clip to thereby removably couple the hook to the elongated member. Other mechanisms for removably coupling the hook to the elongated member are possible as well.

In one embodiment, the elongated member is offset in an anterior plane “AP” and further offset in a lateral plane “LP”.

As used herein, the "anterior plane" indicates a plane that is anterior to the ventral surface of the patient, e.g. ventral to the coronal midaxis of the patient's body. As used herein, the "lateral plane" indicates a plane lateral to the sagittal plane of the patient, e.g. lateral to the sagittal midaxis of the patient's body. The anterior offset and lateral offset are in essence in perpendicular planes to each other. The elongated member transitions at an optimal angle to permit both the transmission of force to the implant and for its use in less invasive surgical procedures. In particular, the elongated member is offset in the anterior plane between about 30 degrees and about 50 degrees, and the elongated member is offset in the lateral plane between about 40 degrees and about 60 degrees. Offset in the anterior plane refers to an angled deviation from the mid-ventral surface of the patient in the coronal plane and offset in the lateral plane refers to an angled deviation from the midline axis of the patient in the sagittal plane, as illustrated in FIGS. 1-4.

In one example, as shown in FIG. 1, the elongated member 150 comprises a first segment 120, a second segment 140, and a third segment 180. The first segment 120 is positioned at the first end of the elongated member 150, the third segment 180 is positioned at the second end of the elongated member 150, and the second segment 140 is positioned between the first segment 120 and the third segment 180. In such an example, the first, second, and third segments are substantially straight and rod-like. The first segment has a length ranging from about 4 cm to about 6 cm, the second segment has a length ranging from about 5 cm to about 7 cm, and the third segment has a length ranging from about 5 cm to about 7 cm. In one example, each of the first, second, and third segments have different lengths. In another example, each of the first, second, and third segments have the same lengths. In another example, the first and second segments have the same length, while the third segment has a different length. In another example, the first and third segments have the same length, while the second segment has a different length. In yet another example, the second and third segments have the same length, while the first segment has a different length.

The cross-sections of the segments 120, 140, 180 can be any convenient shape, such as round, elliptical, square, or rectangular, but typically they will be round. The first segment has a diameter ranging from about 2 cm to about 4 cm, the second segment has a diameter ranging from about 2 cm to about 4 cm, and the third segment has a diameter ranging from about 2 cm to about 4 cm. In one example, each of the first, second, and third segments have different diameters. In another example, each of the first, second, and third segments have the same diameters. In another example, the first and second segments have the same diameter, while the third segment has a different diameter. In another example, the first and third segments have the same diameter, while the second segment has a different diameter. In yet another example, the second and third segments have the same diameter, while the first segment has a different diameter. When the cross-sections are shaped differently than a circle their general size will be the same as described above.

Figure 4A:
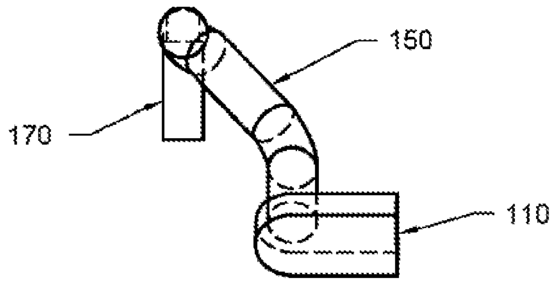
FIGS. 4A-4C illustrates the front view, the right-side view, and the top view of the example device of FIG. 1, respectively, according to an example embodiment.
Figure 4B:
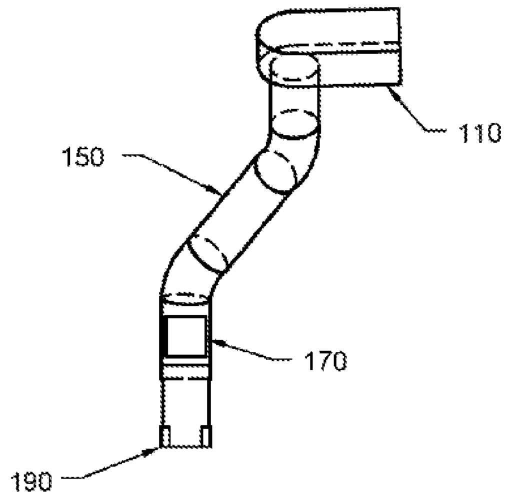
Figure 4C:
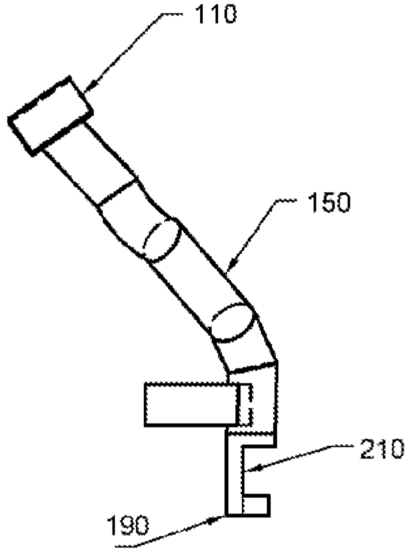
Figure 5B:
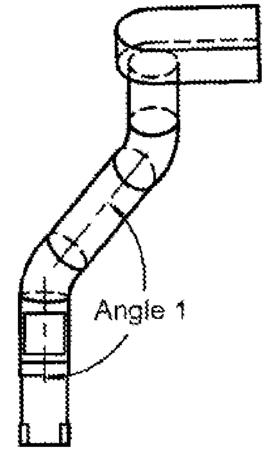
FIGS. 5A-5C illustrate the front view, the right-side view, and the top view of the example device of FIG. 1, respectively, including angles between the various components, according to an example embodiment.
Figure 5C:
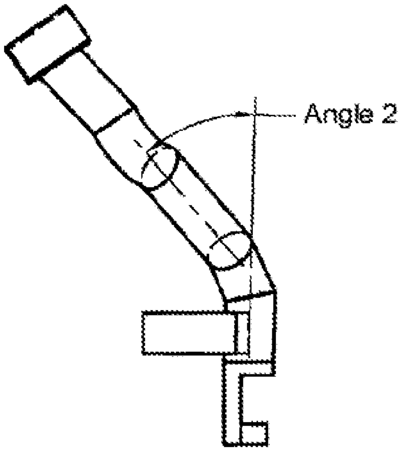
Figure 5A:
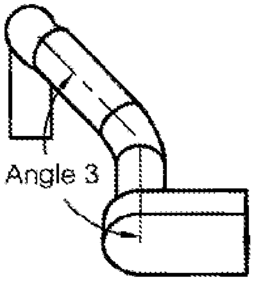
Figure 6:
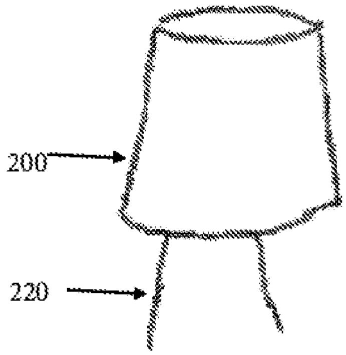
FIG. 6 illustrates an example implant for extraction using the device of FIG. 1, according to an example embodiment.

As shown in FIG. 1, the first 120 and second 140 segments are connected by a first curved segment 130 at their second and first ends, respectively, and the second 140 and third 180 segments being connected by a second curved segment 160 at their second and first ends, respectively. As used herein, "curved" means a segment that is bent at an angle or, more frequently, has a continuously bending centerline. The first 130 and second 160 curved sections provide an offset in an anterior plane and a further offset in a lateral plane. In particular, as shown in FIG. 4, the long axes of the second and third segments are located in a first plane. The angle between the long axis of the third segment and the long axis of the second segment (labeled angle 1 in FIG. 5B) may range from between about 40 degrees and about 60 degrees, which represents an offset in the lateral plane. The first and second segments are located in a second plane that is different than the first plane. The first segment has an angle ranging between about 30 degrees and about 50 degrees with respect to the long axis of the third segment (labeled angle 2 in FIG. 5C) and an angle ranging between about 40 degrees and about 100 degrees with respect to an axis in the first plane that is perpendicular to the long axis of the third segment.

In one particular example, the second segment 140 curves in a direction away from the anterior plane and a direction away from the lateral plane. In one example, the first striking surface 110 extends away from the first segment 120 of the elongated member 150 in a direction substantially perpendicular to the long axis of the first segment 120 and away from the midline axis "M" of the patient as shown in FIG. 1, and the second striking surface 170 extends away from the third segment 180 of the elongated member 150 in a direction substantially perpendicular to the long axis of the third segment 180 and away from the channel 210 in the lock 230. In another example, the first striking surface 110 extends away from the first segment 120 of the elongated member 150 in a direction substantially perpendicular to the long axis of the first segment 120 and away from the midline axis "M" of the patient as shown in FIG. 1, and the second striking surface 170 extends away from the second segment 140 of the elongated member 150 in a direction substantially perpendicular to the long axis of the third segment 180 and away from the channel 210 in the lock 230. Other arrangements are possible as well.

In one example, the device may comprise a kit including two elongated members, one left and one right. Only one elongated member is coupled to the lock at a given time. The left and right elongated members may be mirror images of one another. The left elongated member would be used to extract a surgical implant such as, for example, a femoral implant, positioned in the left hip of a patient, while the right elongated member would be used to extract a surgical implant positioned in the right hip of the patient. In one example, the kit does not include the lock. In another example, the kit includes a single lock. Only one elongated member is coupled to the lock at a given time. The lock may be decoupled from the right elongated member and coupled to the left elongated member when a medical professional extracts a surgical implant positioned in the left hip of a patient. In another example, each of the left and right elongated members includes its own lock as part of the kit.

As discussed above, the elongated member 150 may further include two striking surfaces 110, 170 extending away from the elongated member. In one example, the length of the first striking surface 110 is equal to the length of the second striking surface 170. The length of the first striking surface is measured from a first end to a second end of the first striking surface along a long axis of the first striking surface, and the length of the second striking surface is as measured from a first end to a second end of the second striking surface along a long axis of the second striking surface. In another example, the length of the second striking surface is greater than the length of the second striking surface. The elongated member 150 may have a length ranging from about 15 cm to about 25 cm. As used herein, the length of the elongated member comprises the arc length, or the length of the centerline of the elongated member, from the first end to the second end. The first striking surface 110 may have a length ranging from about 1 cm to about 2 cm, and the second striking surface 170 may have a length ranging from about 7 cm to about 9 cm.

Generally, the first 110 and second 170 striking surfaces comprise a protrusion capable of transferring the force from the impact of a hammer strike to the elongated member 150. More particularly, the first and second striking surfaces comprise a protrusion from the elongated member, preferably principally in a direction perpendicular to a longitudinal line or tangent to a generally longitudinal arc along the length of the hook 190 at the location of the protrusion. In particular, the first striking surface 110 extends away from a long axis of the first segment 120 in a substantially perpendicular direction to the long axis of the first segment 120 at the point at which the first striking surface 110 is positioned, and the second striking surface 170 extends away from a long axis of the third segment 180 in a substantially perpendicular direction to the long axis of the third segment 180 at the point at which the second striking surface 170 is positioned. As such, the long axes of the first and second striking surfaces may be substantially parallel to one another. The first and second striking surfaces can be rounded or comprise a flat surface for receiving hammer strikes. The longitudinal direction of the first and second striking surfaces extends in a direction away from the anterior plane.

The first 110 and second 170 striking surfaces on the elongated member 150 are designed to tolerate and transfer the impact of a strike (e.g., a hammer strike) by the operator and transmit the force to disrupt the prosthetic/bone interface. In one example, the first striking surface may be positioned between the first end of the elongated member and the second striking surface. In another example, the first striking surface may be positioned at the first end of the elongated member. The first striking surface is generally positioned near the first end of the elongated member (e.g., within 5 cm of the first end of the elongated member). The second striking surface may be positioned at the first end of the third segment of the elongated member. As shown in FIG. 1, the second striking surface may be positioned near the second curved segment 160 of the elongated member. The materials that make up the device, including the elongated member 150, the first 110 and second 170 striking surfaces, and the hook 190, would be corrosion resistant stainless steel typical of orthopedic devices, or other metal alloys that allow for sterilization without significant deformation.

The foregoing describes an implant extractor device 100 to facilitate the removal of a femoral component 270 of a hip joint prosthesis, as one particular non-limiting example. Surgical implants 270 have a trunnion 200, neck 220, and shoulder 300 region which are proximal to the stem that is implanted into the proximal medullar cavity of the femur 310. The device described herein may be secured to the stem at the junction of the trunnion 200 and the neck 220 of the implant. The hook contains a channel of sufficient size to receive the neck of the implant, but small enough to deny passage of the trunnion through it. As such, the hook takes advantage of the differential between the size of the trunnion and the size of the neck of the implant. Due to the varying sizes of implant necks, multiple sizes of the hooks would be necessary, hence the modularity and/or adjustability of the hook. In addition, the hook is secured to the elongated member, which is offset in two planes, anteriorly and laterally, permitting the application of the device in an easy, secure, and less invasive manner. The force generated by the operator will then be transmitted efficiently to the implant via the device so as to effect the prosthetic removal.

Figure 14:
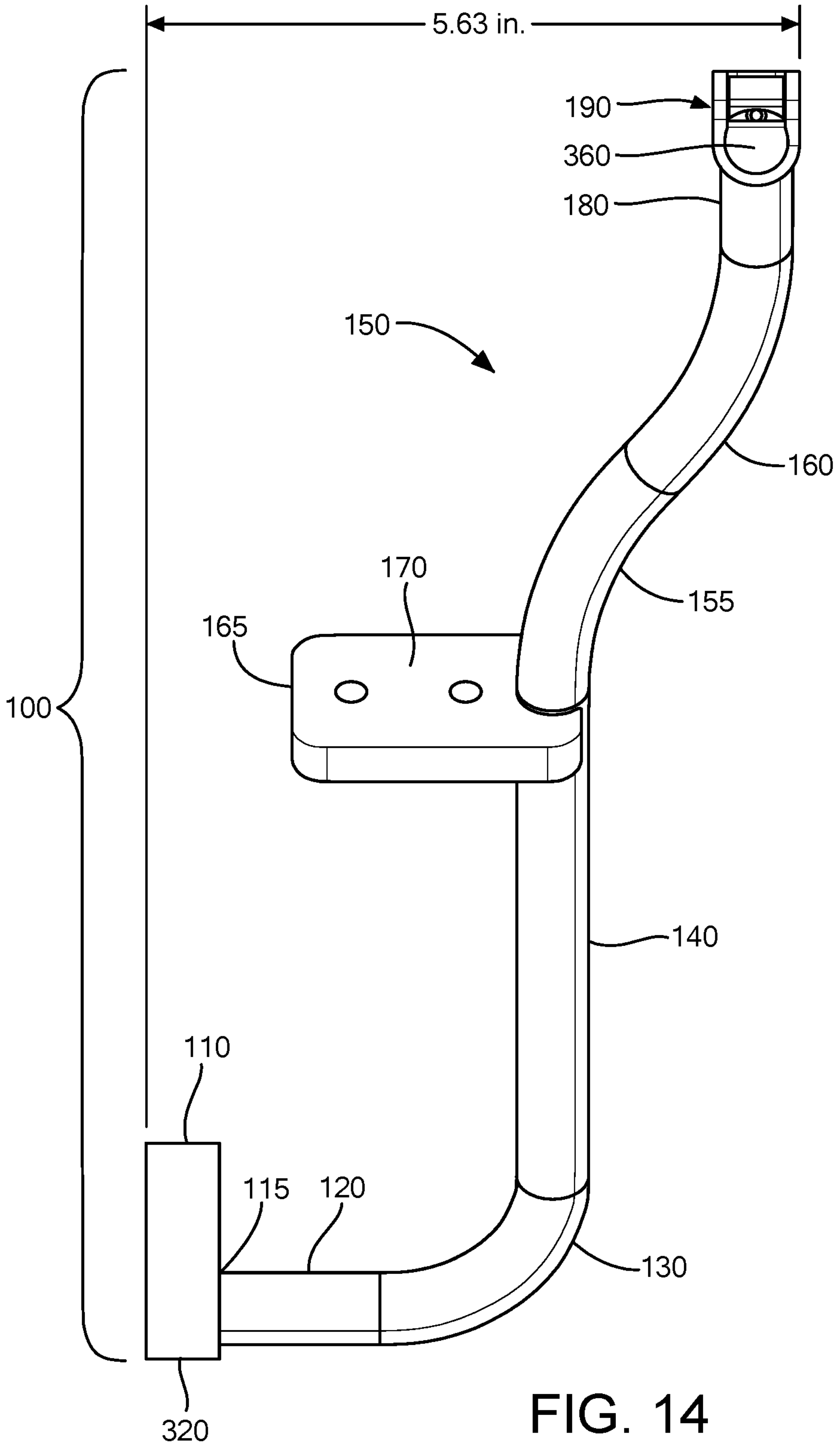
FIG. 14 illustrates a perspective view of another example embodiment of a prosthetic implant extraction device constructed in accordance with the principles of the present application.

Now referring to FIGS. 14-29, another embodiment of a prosthetic implant extraction device 100 is shown. As described herein, the device 100 may also be referred to as a femoral component extractor device. As shown in FIG. 14, the device 100 includes the elongated member 150 which transitions to a handle 320 at the first end 115 of the first segment 120. The area of the device 100 proximate to the first end 115 of the first segment 120 may be referred to as the "first end portion." Additionally, the device 100 has offset in the lateral plane of 5.63 inches or 5.56 inches relative to the lateral aspect of the handle 320. The device 100 also includes the first striking surface 110 positioned on the first segment extending away from the elongated member 150 at a 90-degree angle in a lateral direction, which can also be used as part of the handle 320 to grip the device by the surgeon or operator. In other words, the handle 320 may be used as a strike plate as well and vice-versa. Further, the device 100 has an additional strike plate 165 defining the second striking surface 170 at the junction and transition point of the lateral and anterior offset positions. The strike plate 165 and second striking surface 170 are oriented at 90-degree angle in the lateral direction from the body of the elongated member 150.

Figure 15:
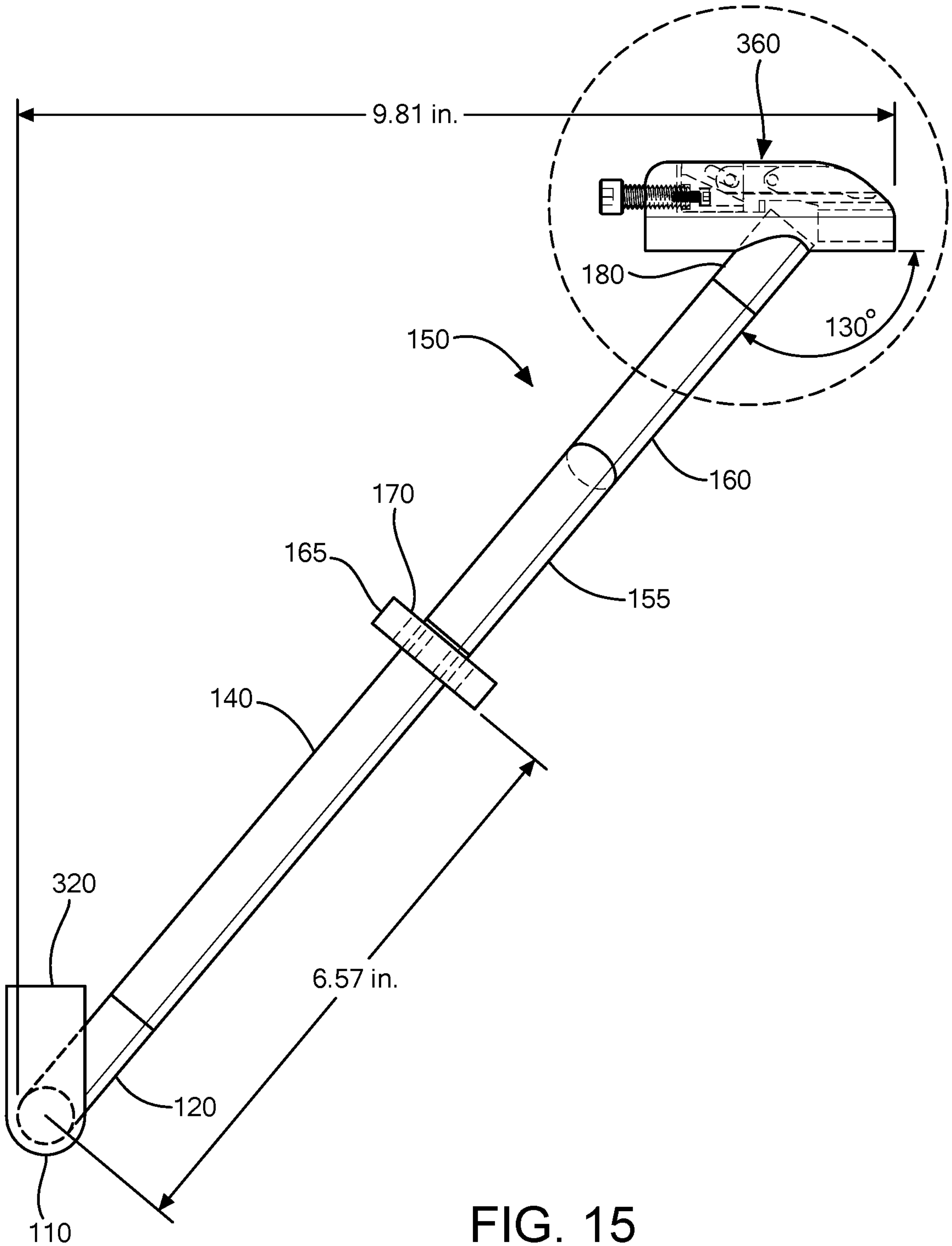
FIG. 15 illustrates a side view of the device of FIG. 14, according to an example embodiment.

FIG. 15 demonstrates a side view of the prosthetic implant extraction device 100. As shown in FIG. 15, the device 100 further includes a hook 190 having a housing 330, positioned at the second end of the third segment 180 opposite the handle 320. The area proximate to the third segment 180 may also be referred to herein as the "distal end portion."

Figure 20A:
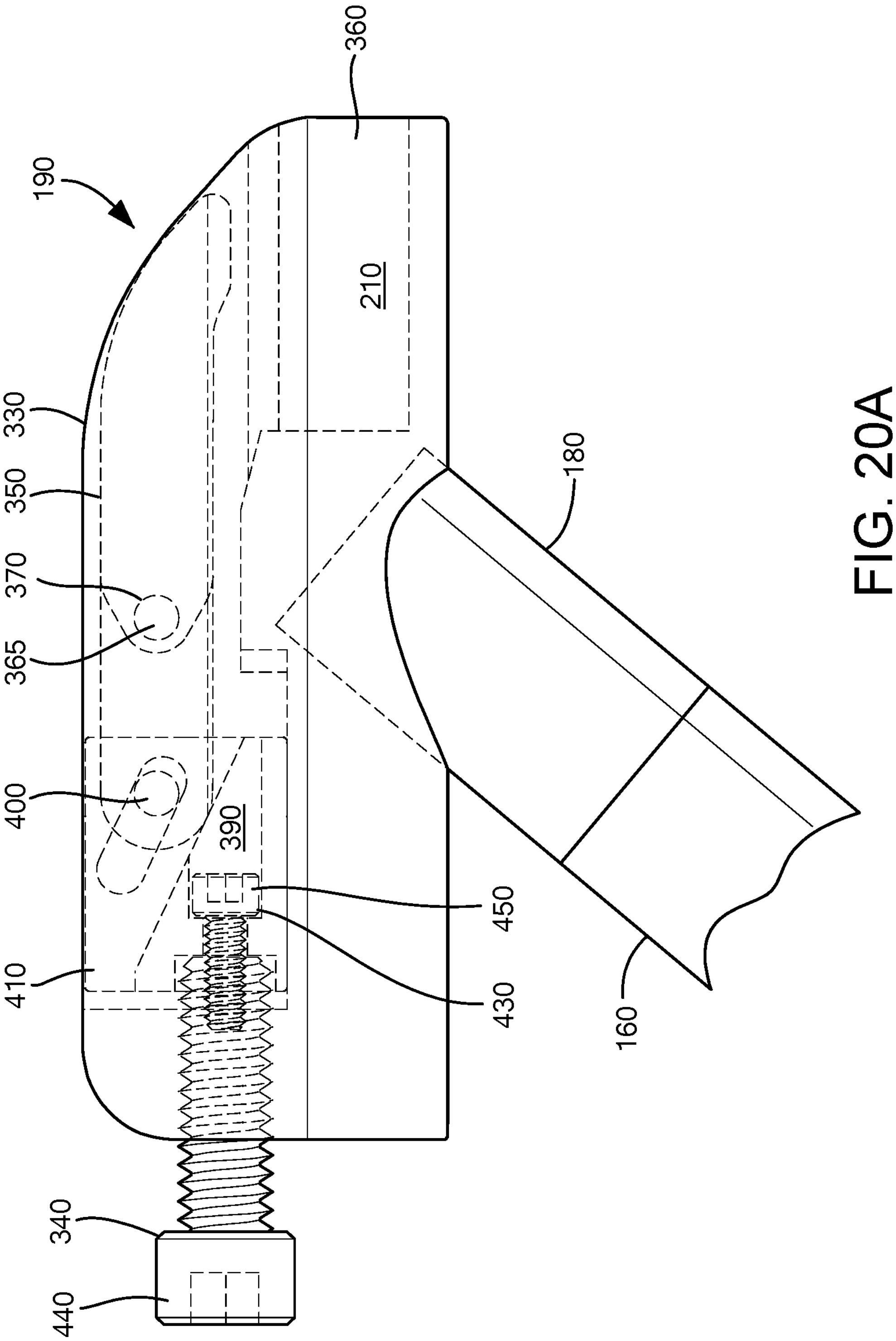
FIG. 20A illustrates a side view of an example hook which is coupled to the elongated member of FIGS. 14-17, according to an example embodiment.

The housing 330 includes the locking channel 210 or opening which is oriented 130 degrees relative to the long axis of the third segment 180. The locking channel 210 is configured to engage and lock onto the surgical implant 270. The strike plate 165, which is located at the transition point of the lateral to the anterior offset, is 6.57 inches from the handle 320 which is located at the first end 115 of the first segment 120. In one or more embodiments, the distance from the locking channel 210 to the most distal portion of the handle 320 is 9.81 inches. The locking channel 210 may be oriented 130 degrees from the plane of the elongated member 150. The locking channel 210, in addition, contains a primary locking bolt 340—such as, for example, a hex bolt or other similar type of bolt—which is operated by the surgeon. As the locking bolt 340 is tightened, it actuates a lever which is engaged at a fixed point around which the locking clamping arm 350 (as shown in FIG. 20A) narrows an aperture 360 of the channel 210 opening thereby securing the trunnion 200 of the surgical implant 270 to the housing 330.

Figure 16:
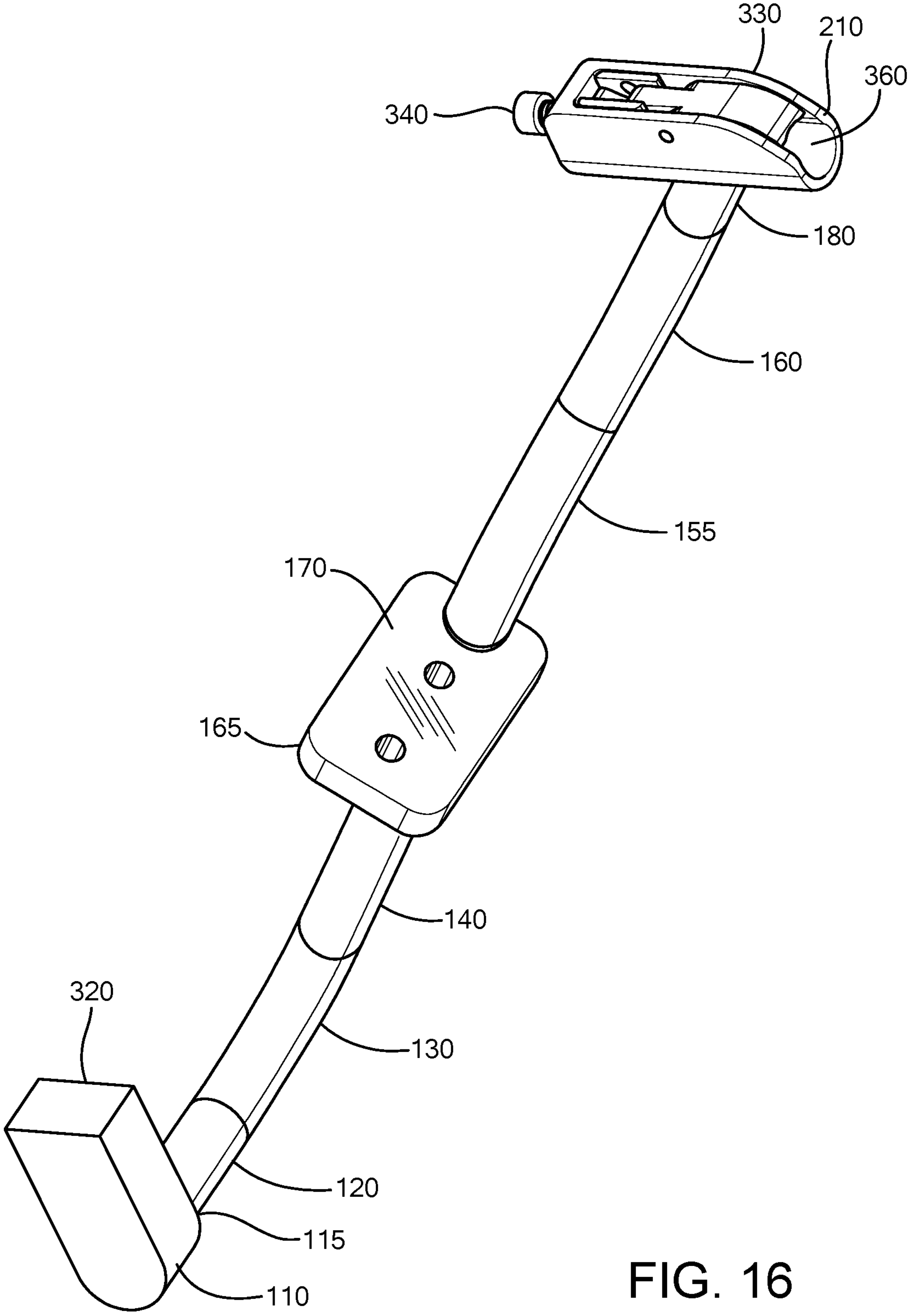
FIG. 16 illustrates a perspective view of the device of FIGS. 14-15, according to an example embodiment.

FIG. 16 demonstrates an additional side view of the device 100. The strike plate 165 extends at a 90-degree angle from the elongated member 150. The locking channel 210 is again demonstrated such that as the primary locking bolt 340 is engaged and tightened by the operator (e.g., surgeon, clinician, etc.) of the device 100, the aperture of the channel 210 is narrowed as the locking clamp arm 350 pivots around the pivot point 370 on the housing 330.

Figure 17:
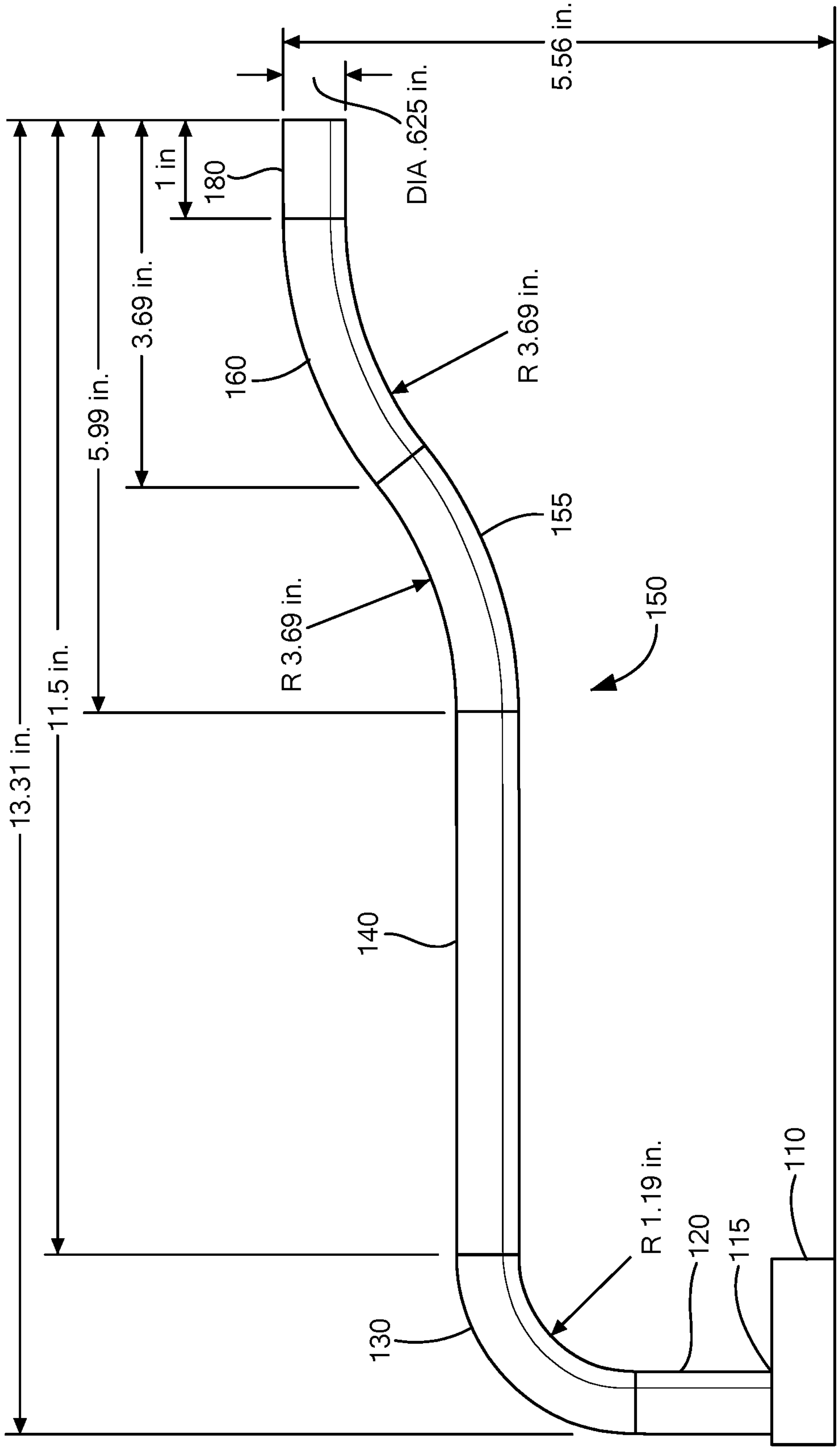
FIG. 17 illustrates a top view of the elongated member of the device of FIGS. 14-16, according to an example embodiment.

FIG. 17 demonstrates a top view of the device 100 identifying the relative dimensions of the device. In one or more embodiments, the device 100 is approximately 13.31 inches in length from the first end 115 of the first segment 120 to the second end 175 of the third segment 180. Additionally, in some such embodiments, the device 100 approximately 5.56 inches or 5.63 inches in length from the proximal end of the housing 330 to the lateral aspect of the first end 115 of the first segment 120. The elongated member 150 is approximately 0.625 inches in diameter. As shown in FIG. 17, the elongated member 150 also includes a second curved segment 155 and a third curved segment 160 coupled to the second curved segment 155. The third curved segment is coupled to the third segment 180 at a first end and coupled to the second curved segment at an opposite second end. As such, the second curved segment 155 is coupled to both the second segment 140 and the third curved segment 160. The third segment 180 and third curved segment 160 together are approximately 3.69 inches in length. The second curved segment 155, third curved segment 160, and third segments 180 together are approximately 5.99 inches length. In addition, the length of the first, second, and third segments 120, 140, 180 exclusive of the handle 320 is 11.5 inches. The top view demonstrates the offset in the lateral plane.

Figure 18B:
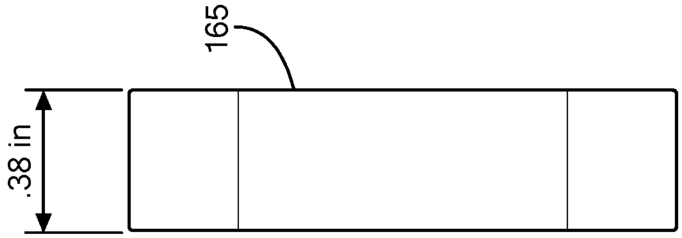
FIG. 18B illustrates a side view of the striking surface of FIG. 18A, according to an example embodiment.
Figure 18A:
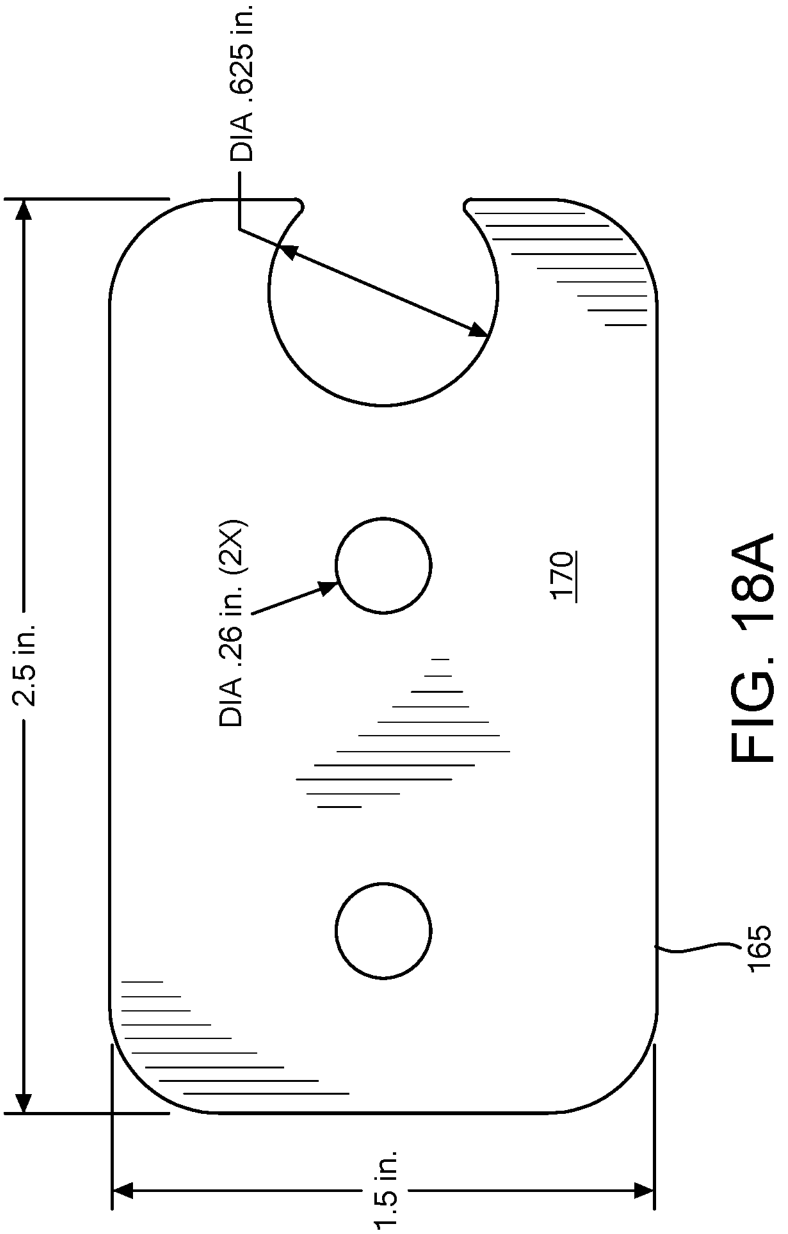
FIG. 18A illustrates a top view of the striking surface of the device of FIGS. 14-16, according to an example embodiment.

FIG. 18A demonstrates a top view of the second striking surface 170 which is approximately 2.5 inches in length in the lateral plane and 1.5 inches in the anterior-posterior plane. As demonstrated in FIG. 18B, the second striking surface 170 is 0.38 inches thick. The second striking surface 170 is on the strike plate 165 which is connected to the elongated member 150 which has a diameter of 0.625 inches at a 90-degree angle oriented in the lateral direction to the elongated member 150.

Figure 19:
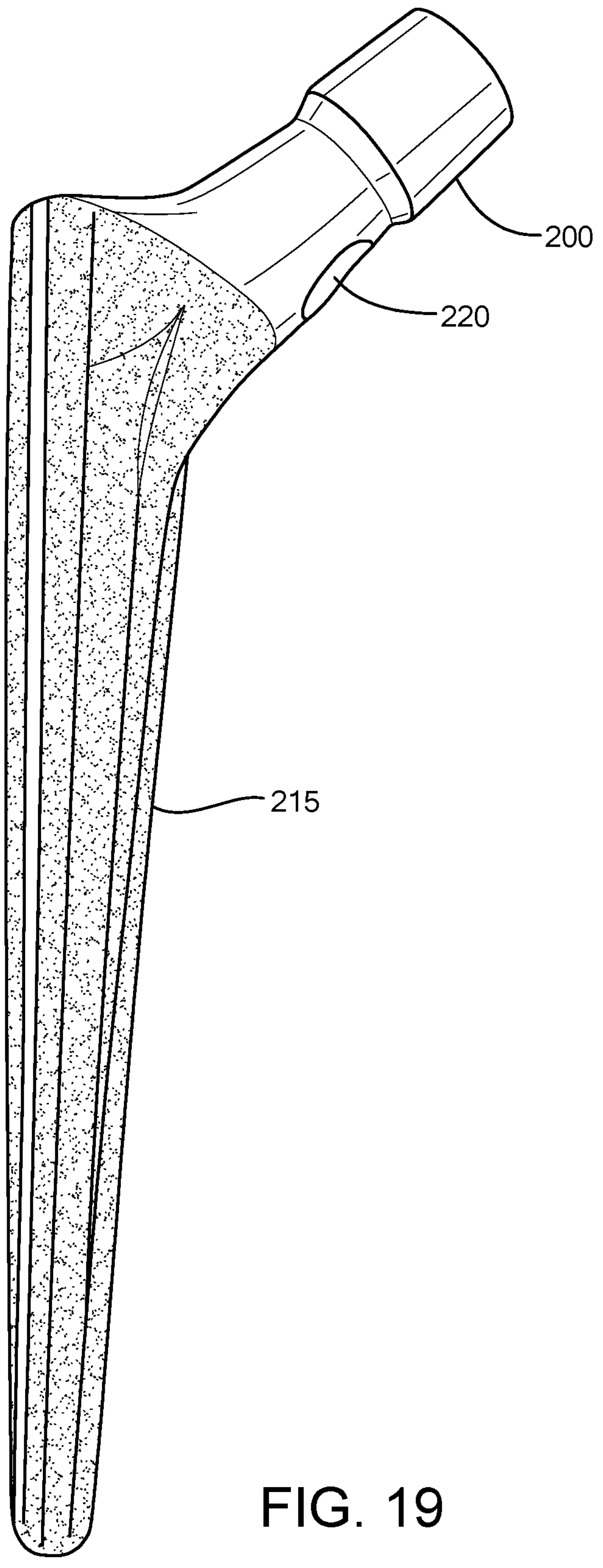
FIG. 19 illustrates a front view of an example surgical implant for use with the device of FIGS. 14-16, according to an example embodiment.

FIG. 19 demonstrates the features of the implant 270. The implant 270 consists of three main components, the body 215, neck 220, and trunnion 200. To couple the implant 270 to the device 100, the trunnion 200 is inserted into the channel 210 of the housing 330 which houses the locking clamping arm 350.

FIG. 20A demonstrates an internal side view of the clamp housing 330 which is attached to the elongated member 150 via a weld seam. The channel 210 has an aperture 360 which accepts the trunnion 200 of the surgical implant 270 as identified in FIG. 19. The salient features of the clamp mechanism include the locking clamp arm 350 which is described in more detail in FIGS. 22A-C (discussed below). The locking clamp arm 350 is mounted for greater stability in a fixed position by a peg 365 at the pivot point 370 which secures the locking clamp arm 350 to the housing 330. The clamping arm 350 secures the trunnion 200 at the aperture 360 of the clamp housing 330 once the primary locking bolt 340 is advanced. It rotates around the pivot point 370 and is actuated by the primary locking bolt 340 which is advanced by the operator. As the operator advances the primary locking bolt 340 it drives an actuating element, such as, for example, wedge block 390, along the undersurface of the clamp arm 350 which closes down the aperture 360. Conversely, retraction of the primary locking bolt 340 produces the retrograde movement of the wedge block 390 and allows for excursion of the clamping arm 350 to open the aperture 360 and release of the trunnion 200. The clamping arm 350 is additionally secured to the housing 330 assembly both at the pivot point 370 and a secondary rotation pin or peg 400 located at the proximal end of the clamping arm 350 which moves to a second position towards secondary rotation pin 400 upon advancement of the wedge block 390 along the undersurface of the clamping arm 350.

Figure 20C:
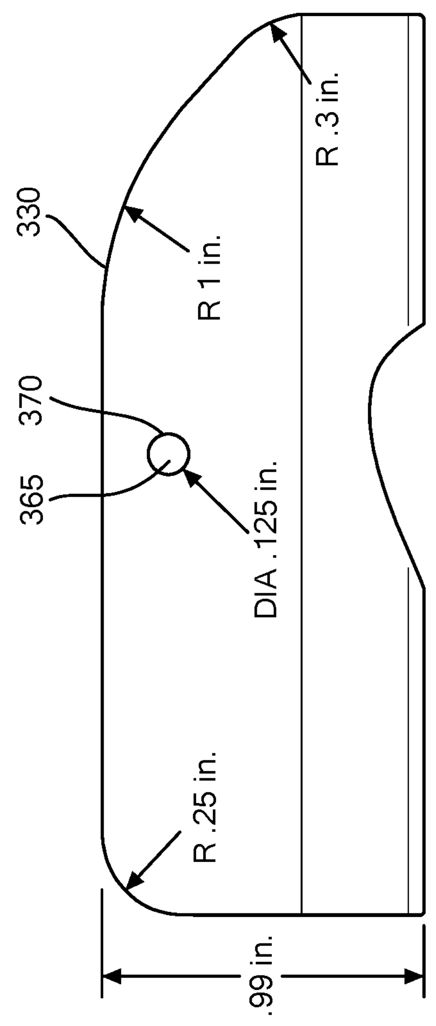
FIG. 20C illustrates a side view of the housing of the hook of FIG. 20A, according to an example embodiment.
Figure 20D:
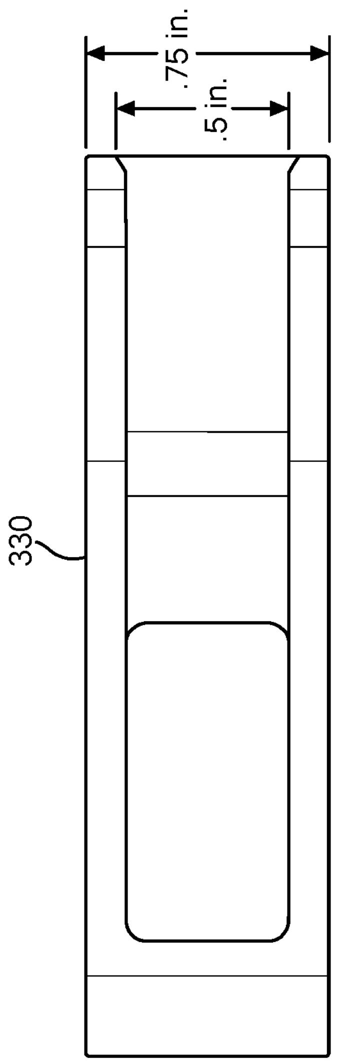
FIG. 20D illustrates a top view of the housing of FIG. 20C, according to an example embodiment.
Figure 20B:
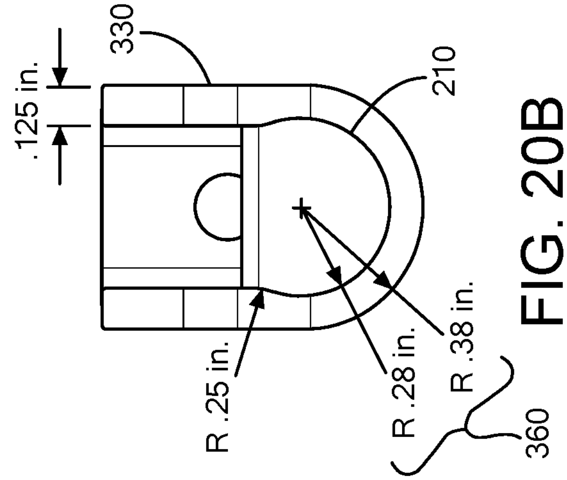
FIG. 20B illustrates an axial view of a channel of the hook of FIG. 20A, according to an example embodiment.

Now referring to FIGS. 20B-20D, FIG. 20B demonstrates the axial view of the channel 210. In one or more embodiments, the channel 210 has a wall thickness of 0.125 inches. Additionally, the wall thickness at the radius of the aperture 360 is approximately 0.38 inches. As demonstrated in FIG. 20C, the clamp housing 330 is 0.99 inches thick. The peg 365 at pivot point 370 around which the clamping arm 350 rotates is 0.125 inches in diameter. FIG. 20D demonstrates the top view of the clamp housing 330 which measures 0.5 inches internally and 0.75 inches including the housing walls.

Figure 21A:
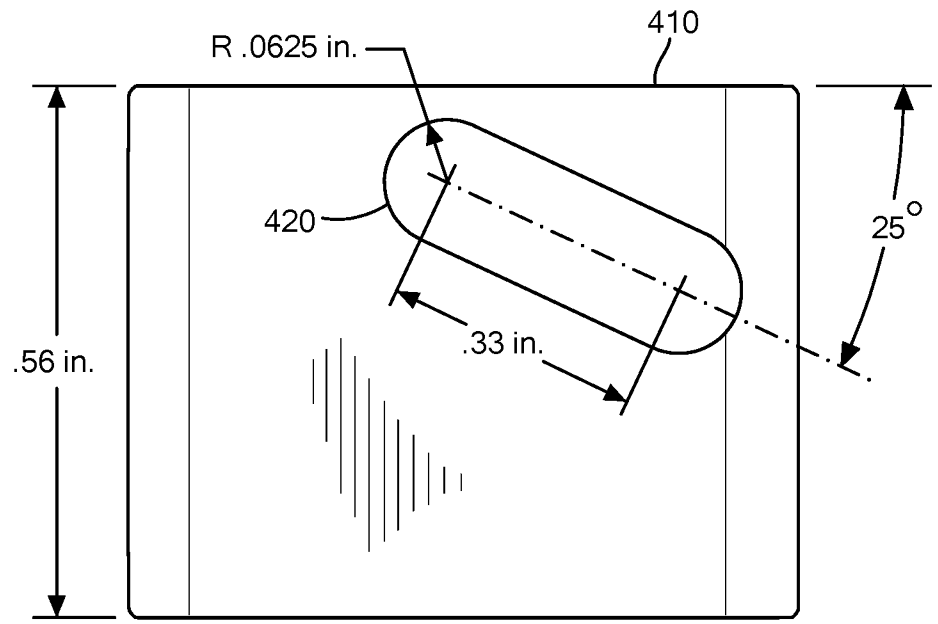
FIGS. 21A-B illustrate a side view of a pin slot block of the hook of FIG. 20A, and the pin slot block containing a secondary pin slot, according to an example embodiment.
Figure 21B:
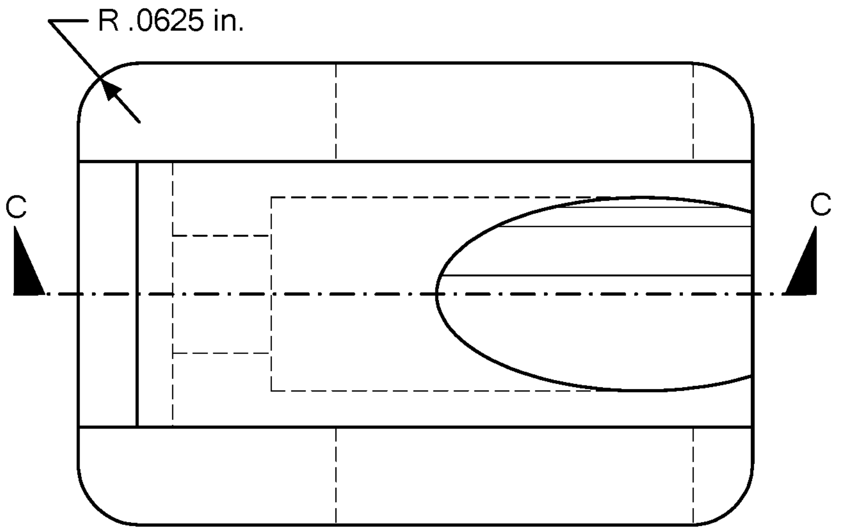
Figure 21C:
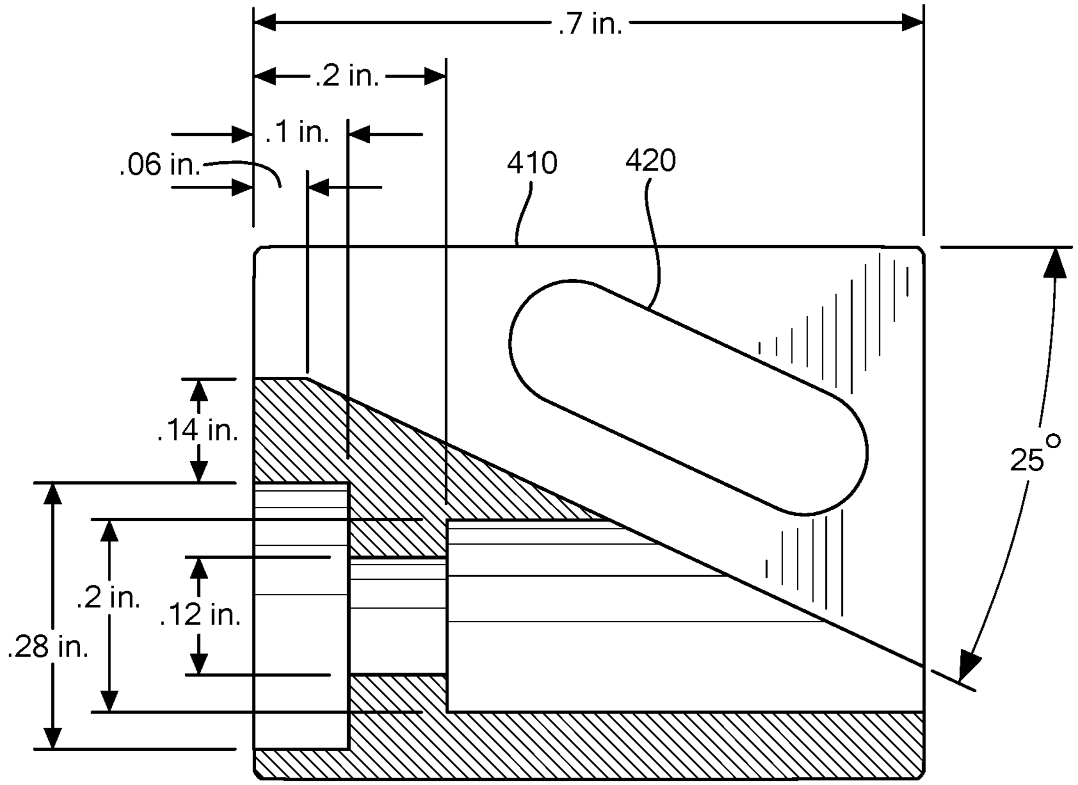
FIG. 21C illustrates the cross-section C-C of FIG. 21B of the pin slot block.

FIGS. 21A-C demonstrates the side (FIG. 21A) view of the pin slot block 410 as it contains the secondary pin slot 420 which has a linear dimension of approximately 0.33 inches and is oriented at a 25-degree angle from the top surface of the block 410. The pin slot block 410 has a height of 0.56 inches and a length of 0.56 inches. The pin slot block 410 engages the secondary pin (not shown) which allows for containment and excursion of the clamping arm 350 along its axis through the pin slot 420. The sliding wedge block 390 actuates the clamping arm 350 as it moves along the pin slot 420 to allow for clamping and release of the clamping arm 350 as it grips and releases the trunnion 200. FIG. 21C is the top view of the pin slot block 410.

Figure 22B:
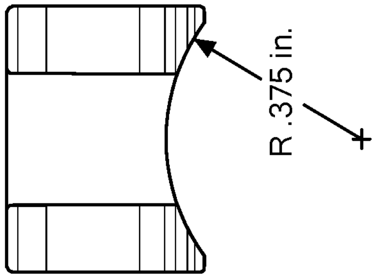
FIG. 22B illustrates an axial view of the clamping arm of FIG. 22A, according to an example embodiment.
Figure 22A:
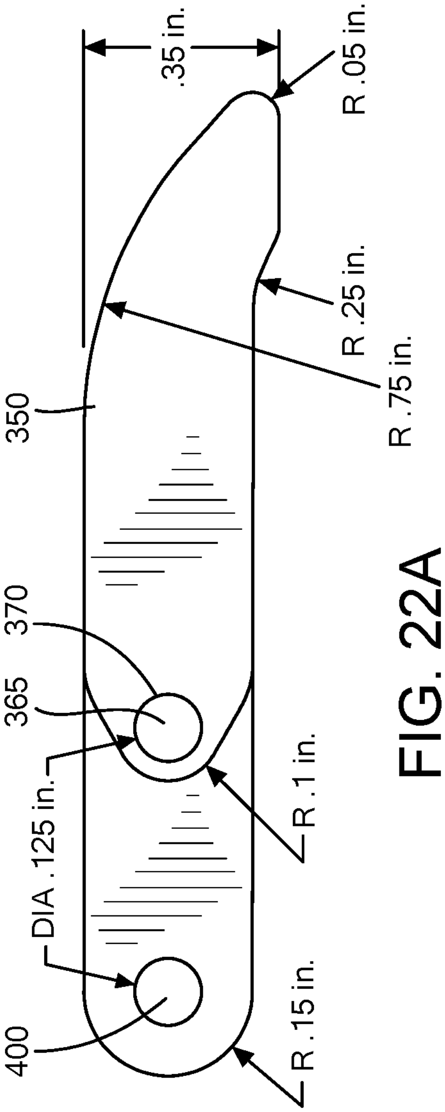
FIG. 22A illustrates a side view of the clamping arm of the hook of FIG. 20A, according to an example embodiment.
Figure 22C:
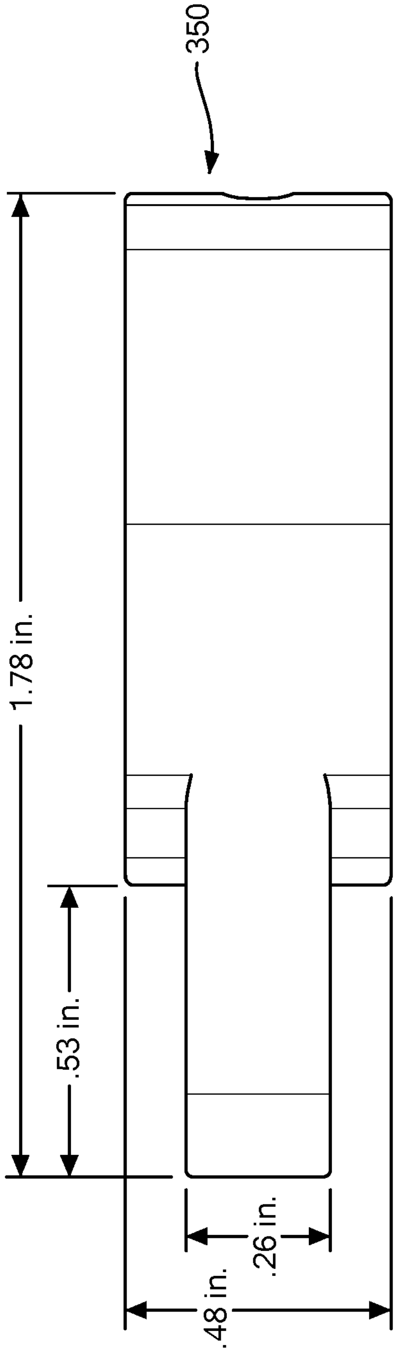
FIG. 22C illustrates a top view of the clamping arm of FIG. 22A, according to an example embodiment.

Now referring to FIGS. 22A-C, the side view (FIG. 22A), axial view (FIG. 22B), and top view (FIG. 22C) of the clamping arm 350 are shown. As shown in FIG. 22A, the pivot point 370 of the clamping arm 350 defines a central hole in which peg 365 may be inserted. As such, the central hole and peg 365 may have a diameter of 0.125 inches at pivot point 370 about which the clamp rotates. The movement around the central rotation axis is actuated by the wedge block 390 as it moves in a proximal-distal axis. The wedge block 390 slides along the undersurface of the clamping arm 350 at its proximal aspect. The distal aspect engages the trunnion 200 and has a concave surface which matches the approximate surface of the trunnion 200. The approximate dimensions of the clamping arm 350 is shown in FIG. 22C which demonstrates that the length of the clamping arm 350 is approximately 1.78 inches and 0.48 inches wide. The region of the clamping arm 350 which is actuated by the movement of the wedge block 390 is approximately 0.26 inches wide and 0.53 inches long.

Figure 23A:
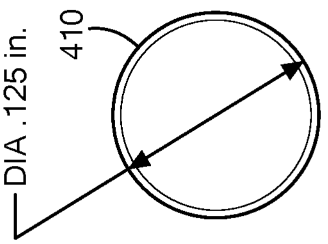
FIG. 23A illustrates an axial view of a secondary rotation pin which engages the pin slot block of FIGS. 21A-C, according to an example embodiment.
Figure 23B:
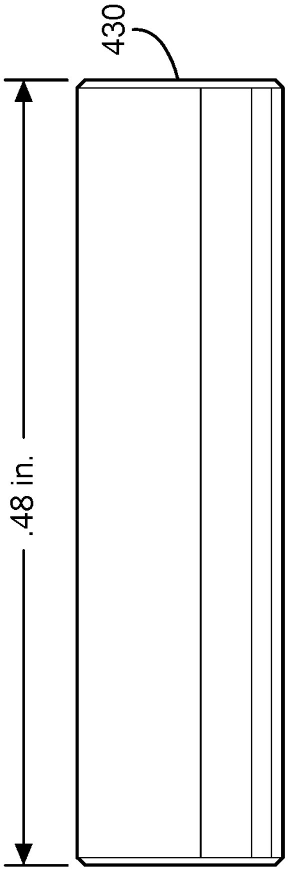
FIG. 23B illustrates a side view of the secondary rotation pin of FIG. 23A which engages the pin slot block of FIGS. 21A-C, according to an example embodiment.

FIGS. 23A-B demonstrate the axial (FIG. 23A) and side (FIG. 23B) views of the secondary rotation pin 400 which engages the pin slot block 410.

Figure 24A:
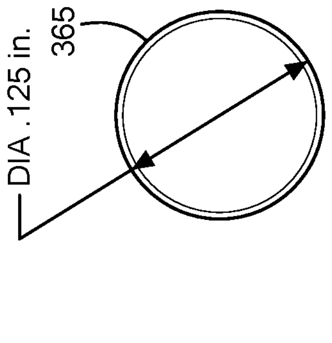
FIG. 24A illustrates an axial view of the primary rotation pin of the hook of FIG. 20A, according to an example embodiment.
Figure 24B:
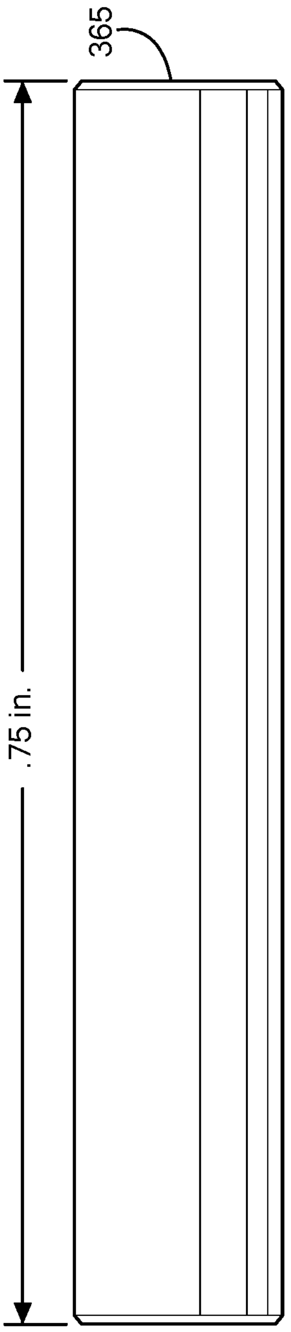
FIG. 24B illustrates a side view of the primary rotation pin of FIG. 24A, according to an example embodiment.

FIGS. 24A-B demonstrate the axial (FIG. 24A) and side (FIG. 24B) views of the rotational peg 365 which is the axis point for rotation of the clamping arm 350 as it is actuated by the sliding wedge block 390.

Figure 25A:
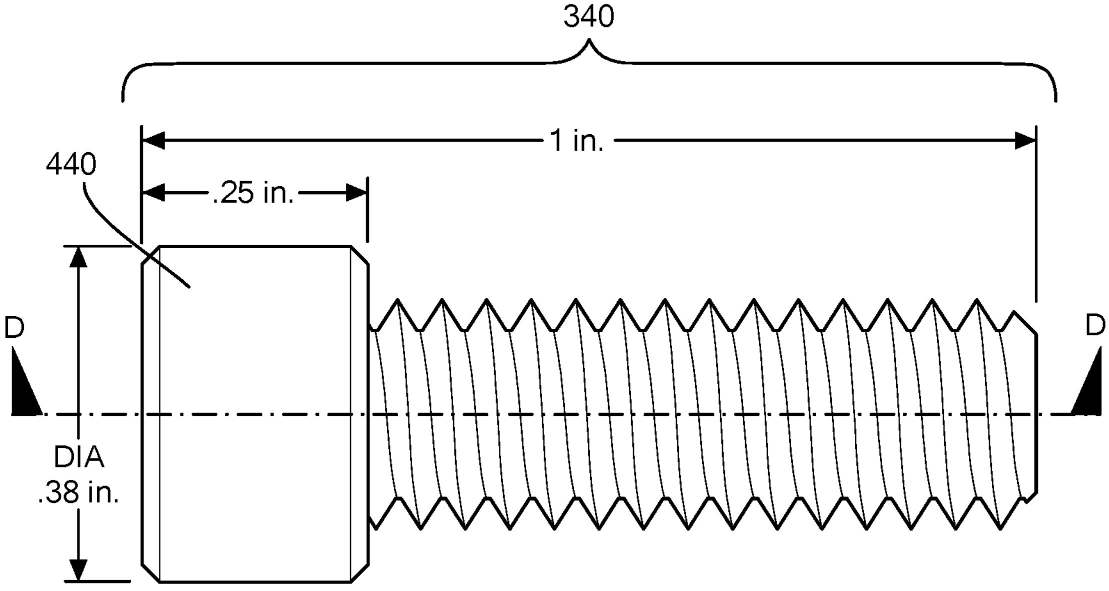
FIG. 25A illustrates a side view of the primary locking bolt of the hook of FIG. 20A, according to an example embodiment.
Figure 25B:
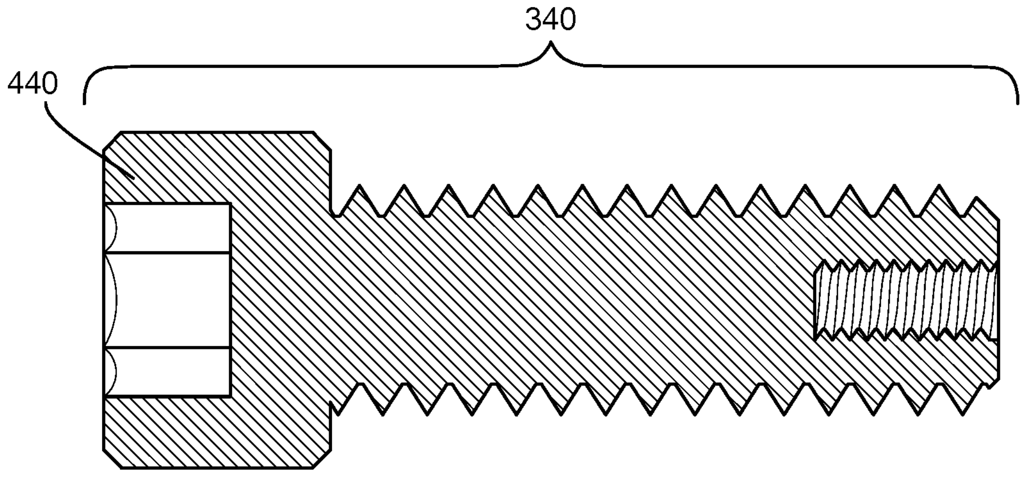
FIG. 25B illustrates a sectional view of the primary locking bolt of FIG. 25A, according to an example embodiment.

Now referring to FIGS. 25A-B, side views of the primary locking bolt 340 which is operated by the surgeon via the hex screwdriver, or other device with a corresponding mating member, are shown. The primary locking bolt 340 drives a secondary locking bolt 430 which is attached to the wedge block 390. As the primary locking bolt 340 is advanced, the secondary locking bolt 430 advances the wedge block 390 which actuates the clamping arm 350 via the fulcrum acting through the rotational peg 365 at pivot point 370 as identified in FIG. 20A. As the wedge block 390 is advanced, the clamping arm 350 closes down the aperture 360 of the housing 330 securing the trunnion 200 of the surgical implant in the housing 330. Conversely, loosening the primary locking bolt 340, retracts the secondary locking bolt 430 and the attached wedge block 390. The retrograde motion of the wedge block 390, loosens the clamping arm 350 and releases the trunnion 200 from the housing 330. In one or more embodiments, primary locking bolt 340 measures 1 inch in length. The head 440 of the primary locking bolt 340 measures 0.25 inches in thickness and 0.38 inches in diameter. As described herein, the primary locking bolt 340 and secondary locking bolt 430 may each be referred to as primary or secondary "retaining mechanisms."

Figure 26A:
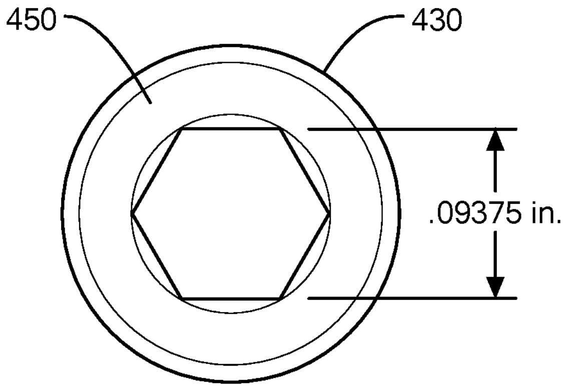
FIG. 26A illustrates an axial view of a secondary locking bolt of the hook of FIG. 20A, according to an example embodiment.
Figure 26B:
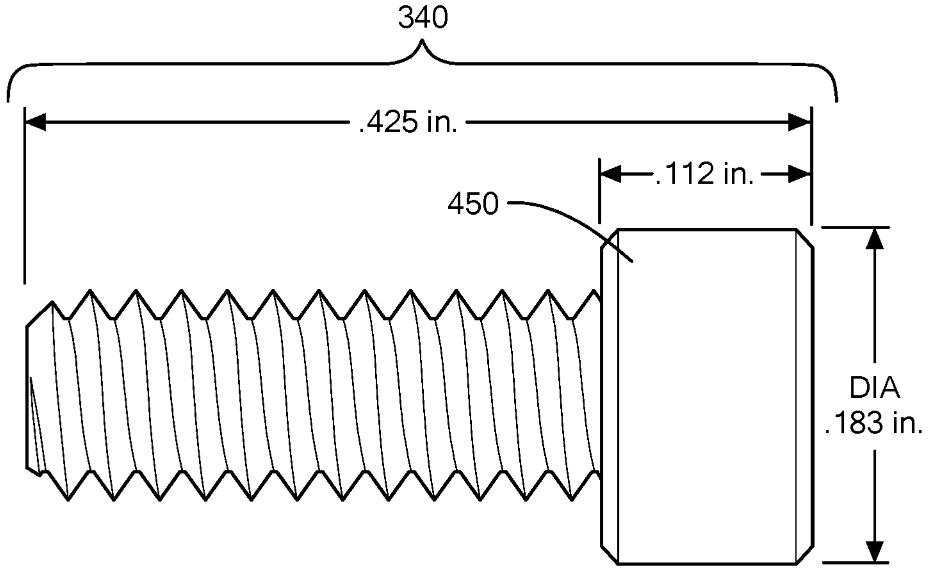
FIG. 26B illustrates a side view of the secondary locking bolt of FIG. 26A, according to an example embodiment.

Now referring to FIGS. 26A and 26B, the axial (FIG. 26A) and side (FIG. 26B) view of the secondary locking bolt 430 which is attached to the wedge block 390 as demonstrated in FIG. 20A are shown. The secondary locking bolt 430 measures 0.09375 inches in diameter. The head 450 of the secondary locking bolt 430 has a width of 0.183 inches and a thickness of 0.112 inches. The length of the secondary locking bolt 430 is 0.425 inches.

Figure 27:
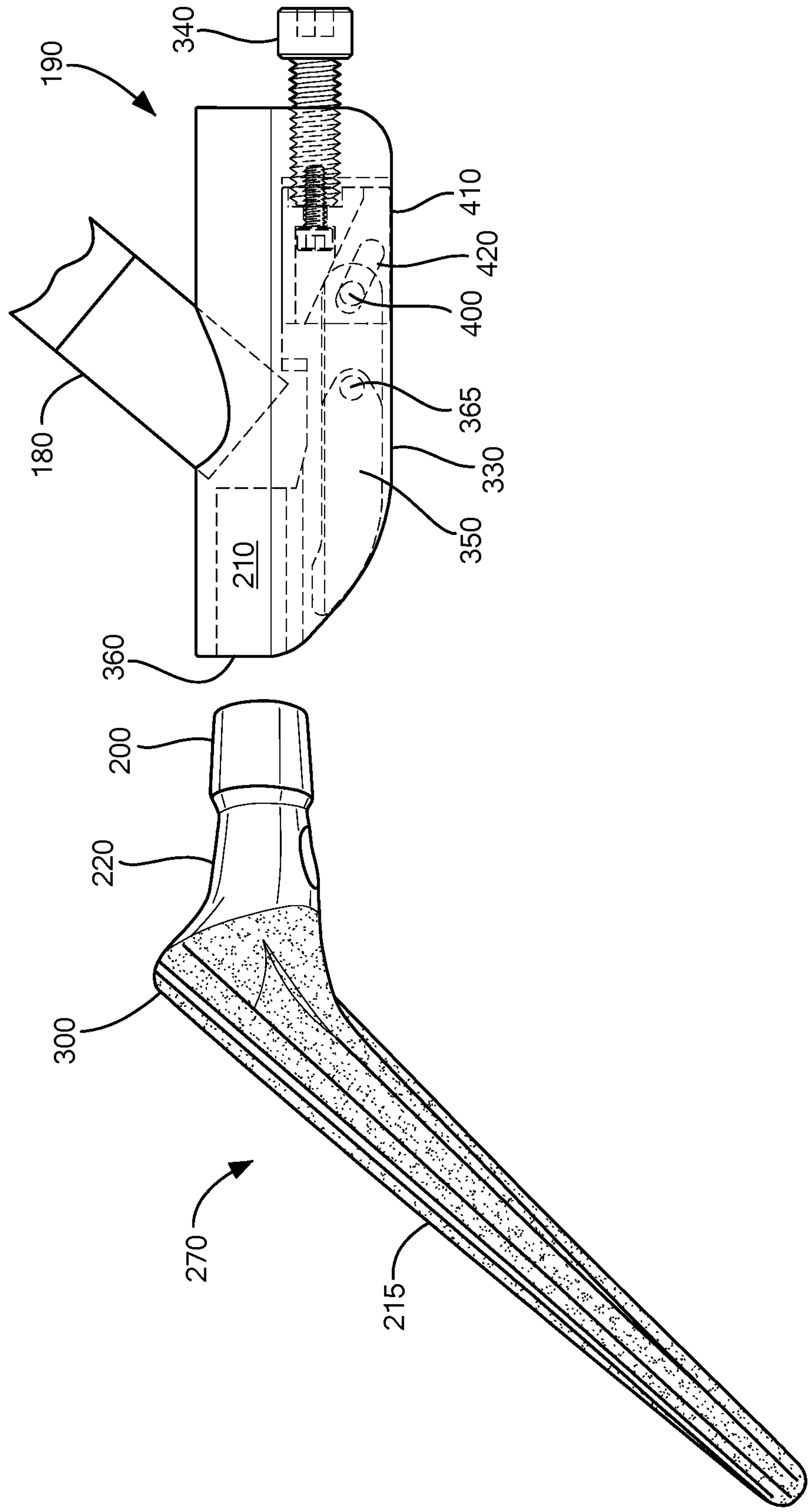
FIG. 27 illustrates a side view of the device of FIGS. 14-16 prior to inserted of the surgical implant into the housing of the hook, according to an example embodiment.

FIG. 27 demonstrates the side view of a surgical implant 270 prior to insertion of the trunnion 200 into the housing 330. It additionally demonstrates the clamping arm 350 in the open position. The trunnion 200 is inserted into the housing 330 and the primary locking bolt 340 is advanced thereby closing the aperture 360 of the housing 330.

Figure 28A:
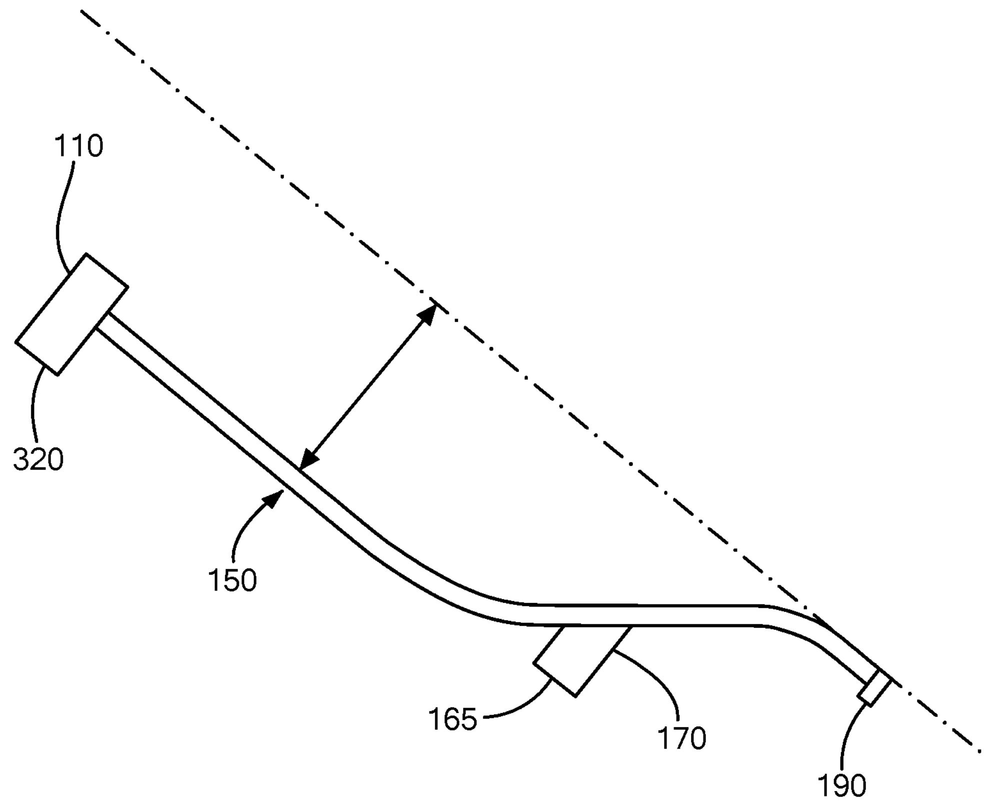
FIG. 28A illustrates a side view of the device of FIGS. 14-16 according to another example embodiment constructed in accordance with the principles of the present application.
Figure 28B:
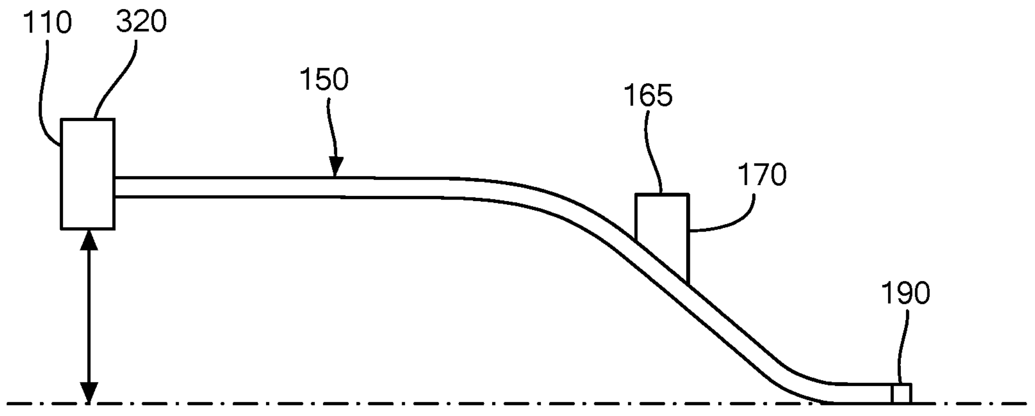
FIG. 28B illustrates a top view of the device of FIG. 28A, according to an example embodiment.

Now referring to FIGS. 28A and 28B, FIG. 28A demonstrates another embodiment of the elongated member 150 for use with a patient's left hip. In such an embodiment, the offset is oriented in the anterior plane. FIG. 15B demonstrates the top view of the elongated member where the offset is oriented in the lateral plane.

Figure 29:
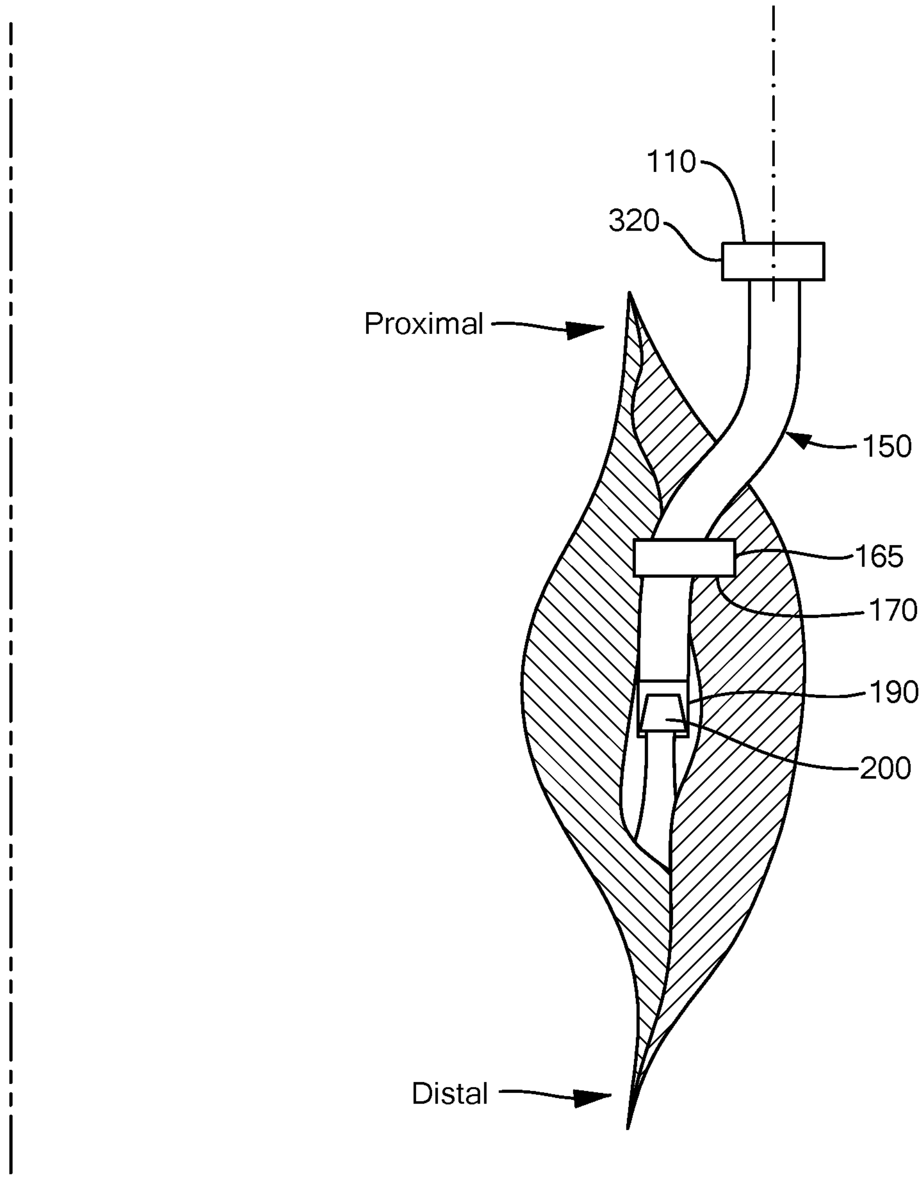
FIG. 29 illustrates a top view of a target treatment area where the elongated member is attached to the trunnion of the implant, according to an example embodiment.

FIG. 29 demonstrates the top view of a left hip where the elongated member 150 is attached to the trunnion 200 of a hip prosthesis. The elongated member 150 is offset in the lateral plane to afford access to the hip prosthesis and placement of the strike plates in a lateral offset position.

It is to be understood that as in the embodiments shown in FIGS. 14-29, the device 100 has a lower profile configuration of the clamping mechanism. Because it is somewhat smaller in its overall dimensions, the device 100 affords a slimmer and less bulky clamp to the trunnion of the femoral component without compromising grip strength. The offsets both in the lateral and anterior planes are additionally somewhat smaller which allows for less soft tissue anatomic dissection during the revision arthroplasty procedure. In addition, the overall weight of the elongated member 150 is thus reduced which puts less stress on the junction to the femoral component and allows for a more facile adaptation of the extractor to the femur and thereby reduces the risk of iatrogenic intraoperative fracture.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A hook assembly for use with a medical device, the assembly comprising:

a housing, the housing defining a channel sized and configured to receive at least a portion of a surgical implant;

a clamping arm coupled to the housing at a pivot point and configured to secure the surgical implant to the housing;

an actuating element disposed within the housing and configured to move in a proximal-to-distal direction along an axis;

a primary retaining mechanism releasably coupled to the housing;

a secondary retaining mechanism disposed within the housing and releasably coupled to the primary retaining mechanism; and wherein:

when the actuating element moves in the proximal-to-distal direction, the clamping arm is configured to rotate about the pivot point;

the secondary retaining mechanism is configured to engage the actuating element within the housing; and the primary retaining mechanism and the secondary retaining mechanism are configured to advance towards a center of the housing when rotational force is exerted on the primary retaining mechanism by a user.

2. The hook assembly of claim 1, wherein advancement of the secondary retaining mechanism within the housing causes the actuating element to move in the proximal-to-distal direction.

3. The hook assembly of claim 2, wherein the actuating element is a wedge block and the secondary retaining mechanism is a secondary locking bolt.

4. The hook assembly of claim 2, wherein the surgical implant is a femoral implant having a body, a neck, and trunnion.

5. The hook assembly of claim 2, wherein:

the housing further defines an aperture;

advancement of the actuating element towards a center of the housing causes the clamping arm to secure the trunnion of the surgical implant; and retraction of the actuating element away from the center of the housing causes the clamping arm to release the trunnion.

6. The hook assembly of claim 5, wherein a wall thickness of the housing, where the aperture is defined, is approximately 0.38 inches.

7. The hook assembly of claim 1, wherein the housing has a wall thickness of approximately 0.125 inches where it defines the channel.

* * * * *